United States Patent [19]

Lampropoulos et al.

[11] Patent Number: 5,209,732
[45] Date of Patent: May 11, 1993

[54] LOCKING SYRINGE WITH THREAD-RELEASE LOCK

[75] Inventors: Fred P. Lampropoulos; Philip M. Triolo, both of Salt Lake City; William Padilla, Bennion, all of Utah

[73] Assignee: Merit Medical Systems, Inc., Salt Lake City, Utah

[21] Appl. No.: 664,984

[22] Filed: Mar. 4, 1991

Related U.S. Application Data

[63] Continuation-in-part of Ser. No. 434,461, Nov. 13, 1989, Pat. No. 5,047,015, which is a continuation-in-part of Ser. No. 325,561, Mar. 17, 1989, Pat. No. 5,057,078.

[51] Int. Cl.$^5$ ............................................. A61M 29/00
[52] U.S. Cl. ....................................... 604/99; 604/98; 604/224; 606/194
[58] Field of Search ............................... 604/96–100, 604/103, 109, 118, 220, 224, 225, 227, 207–208; 606/191, 192, 194; 128/675

[56] References Cited

U.S. PATENT DOCUMENTS

| | | |
|---|---|---|
| 404,105 | 5/1889 | Overlach. |
| 466,125 | 2/1891 | Schirmer. |
| 577,682 | 2/1897 | Eissner. |
| 730,054 | 6/1903 | Sheets. |
| 1,661,818 | 3/1928 | Cook. |
| 1,707,880 | 4/1929 | Sheets. |
| 2,656,836 | 10/1953 | Hickey ................................ 128/218 |
| 2,672,866 | 3/1954 | Kater .................................. 128/218 |
| 2,699,168 | 1/1955 | Lewis .................................. 128/218 |
| 2,724,385 | 11/1955 | Lockhart ............................. 128/261 |
| 2,736,315 | 2/1956 | Feeney ................................ 128/218 |
| 2,764,978 | 10/1956 | Everett ............................... 128/215 |
| 3,080,866 | 3/1963 | Friedman ............................ 128/218 |
| 3,388,941 | 6/1968 | Marcus .................................... 294/4 |
| 3,478,937 | 11/1969 | Solowey ............................. 222/386 |
| 3,491,757 | 1/1970 | Arce .................................... 128/221 |
| 3,529,596 | 9/1970 | Garner ............................. 128/145.6 |
| 3,884,229 | 5/1975 | Raines et al. ..................... 128/221 |
| 3,931,822 | 1/1976 | Marici ................................ 128/351 |
| 4,057,050 | 11/1977 | Sarstedt ............................. 128/2 F |
| 4,063,662 | 12/1977 | Drummond et al. ................. 222/31 |

(List continued on next page.)

FOREIGN PATENT DOCUMENTS

| | | |
|---|---|---|
| 545415 | 8/1957 | Canada. |
| 0119296 | 9/1984 | European Pat. Off.. |
| 1242737 | 8/1960 | France. |
| 2083364A | 3/1982 | United Kingdom. |

OTHER PUBLICATIONS

"ACS Accessories Offer Optimum Efficiency in Your Angioplasty Procedures," Eli Lilly and Company.

(List continued on next page.)

Primary Examiner—C. Fred Rosenbaum
Assistant Examiner—Chalin Smith
Attorney, Agent, or Firm—Workman Nydegger Jensen

[57] ABSTRACT

A locking syringe selectively operable in either of a freely reciprocating or a restricted, threaded mode. A trigger attached to the plunger includes internal threads on the interior of the barrel of the syringe and external threads located on the plunger on a spine slidable in a longitudinal slot in the plunger. A handle is affixed to the plunger, and a retraction bar is rigidly secured to the spine. The threads on the plunger may be retracted from engagement with the threads on the barrel, thereby placing the syringe in its freely reciprocating mode. The trigger, which is spring biased to engage the external and internal threads, employs a plurality of ramps and channels disposed at approximately the same angle to the longitudinal axes of the plunger and barrel as are the threads. A pawl is pivotally securable on the retraction bar at a position receivable into a pawl receiving aperture on the handle when the receiving bar is in its first position permitting reciprocating movement of the plunger. In this position, the pawl prevents the retraction bar from returning to its second position in which free movement of the plunger is precluded. Alternatively, toward the same end an open, a circumferential clip can be placed on the plunger to restrain sliding of the spine disposed therein, or a plug can be inserted into an aperture in the handle occupied by the retraction bar in its first position.

75 Claims, 10 Drawing Sheets

U.S. PATENT DOCUMENTS

| | | |
|---|---|---|
| 4,106,002 | 8/1978 | Hogue, Jr. ............... 340/626 |
| 4,182,344 | 1/1980 | Benson ............... 128/207.15 |
| 4,254,773 | 3/1981 | Waldbillig ............... 128/348 |
| 4,267,846 | 5/1981 | Kontos ............... 128/765 |
| 4,285,340 | 8/1981 | Gezari et al. ............... 128/205.24 |
| 4,323,071 | 4/1982 | Simpson et al. ............... 128/343 |
| 4,370,982 | 2/1983 | Reilly ............... 604/98 |
| 4,439,185 | 3/1984 | Lundquist ............... 604/97 |
| 4,444,335 | 4/1984 | Wood et al. ............... 222/43 |
| 4,466,426 | 8/1984 | Blackman ............... 128/1.1 |
| 4,504,268 | 3/1985 | Herlitze . |
| 4,526,196 | 7/1985 | Pistillo ............... 137/557 |
| 4,568,335 | 2/1986 | Updike et al. ............... 604/211 |
| 4,573,978 | 3/1986 | Reilly ............... 604/240 |
| 4,583,917 | 4/1986 | Shah ............... 417/63 |
| 4,583,974 | 4/1986 | Kokernak ............... 604/211 |
| 4,601,701 | 7/1986 | Mueller, Jr. ............... 604/83 |
| 4,651,783 | 3/1987 | Demer et al. ............... 128/344 |
| 4,710,179 | 12/1987 | Haber ............... 604/211 |
| 4,715,854 | 12/1987 | Vaillancourt ............... 604/191 |
| 4,723,938 | 2/1988 | Goodin et al. ............... 604/99 |
| 4,743,230 | 5/1988 | Nordquest ............... 604/97 |
| 4,758,223 | 7/1988 | Rydell ............... 604/90 |
| 4,781,192 | 11/1988 | Demer ............... 128/344 |
| 4,787,429 | 11/1988 | Valentini et al. ............... 141/383 |
| 4,819,637 | 4/1989 | Dormandy ............... 128/325 |
| 4,825,876 | 5/1989 | Beard ............... 128/675 |
| 4,832,692 | 5/1989 | Box et al. ............... 604/99 |
| 4,838,684 | 6/1989 | Peterson ............... 604/100 |
| 4,858,615 | 8/1989 | Meinema ............... 128/668 |
| 4,872,483 | 10/1989 | Shah ............... 137/557 |
| 4,877,035 | 10/1989 | Bogen et al. ............... 128/673 |
| 4,896,671 | 1/1990 | Cunningham et al. ............... 128/642 |
| 4,901,731 | 2/1990 | Millar ............... 128/675 |
| 4,919,121 | 4/1990 | Rydell et al. ............... 604/97 |
| 4,940,459 | 7/1990 | Noce ............... 604/97 |

OTHER PUBLICATIONS

Advertising brochure on North American Instrument Corporation entitled "The NAMIC 10cc Angiographic Syringe Features".

Advertising brochure of Spectramed, Inc.; produce prochure for "CONTROLEASE Disposable Control Syringe"; and product brochure for control syringe of COEUR Laboratories, Inc.

"Clearing the Path for a Healthy Heart," *Tristate: The Cincinnati Enquirier Magazine*, Oct. 23, 1988.

"Coronary Angioplasty," Krames Communications, 1985.

"Good News for People with Only Tow Hands," SciMed Life Systems, Inc.

"Health–Critics of Angioplasty Worry About Inflated Success Claims," *U.S. News & World Report*, Jul. 25, 1988, p. 65.

"Inflation PRO: A New Dual-Support System for Angioplasty," Baxter Healthcare Corporation.

"PTCA Safe and Efficacious Performed Together With Diagnostic Angiography in Selected Cases," *Cardiovascular News*, May 1988, p. 8.

"USCI Wizard Disposable Inflation Device," C. R. Bard, Inc.

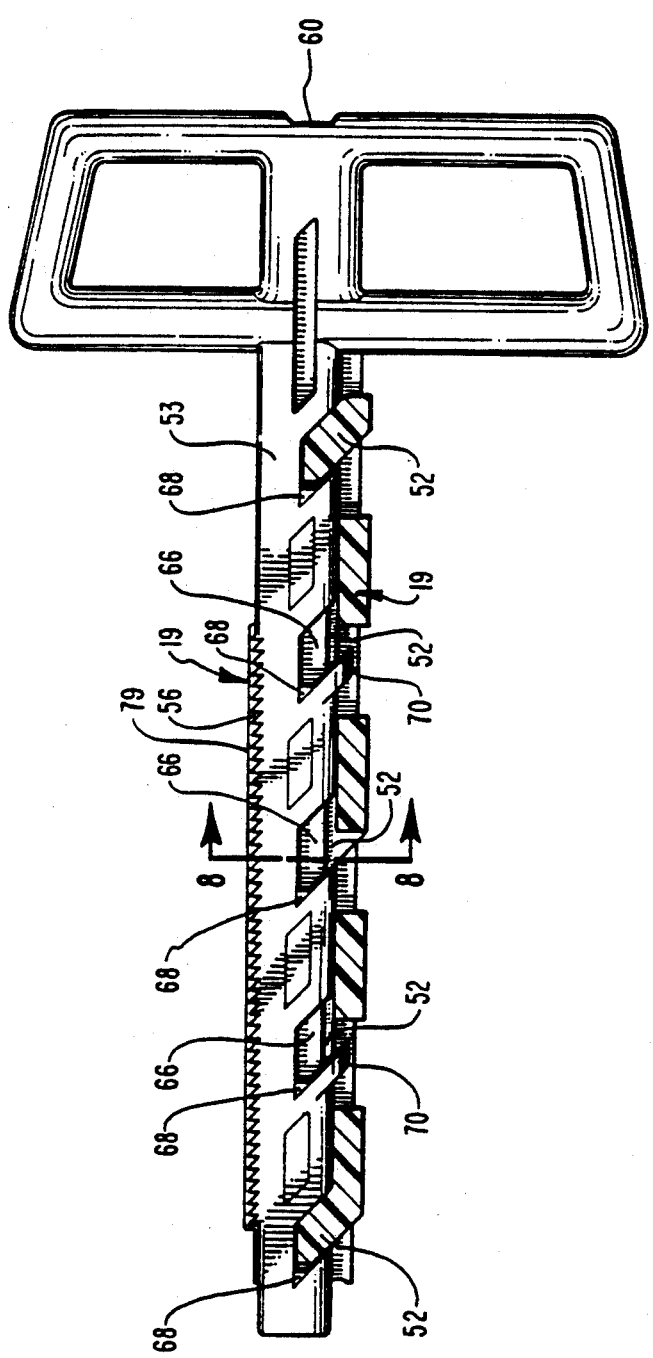
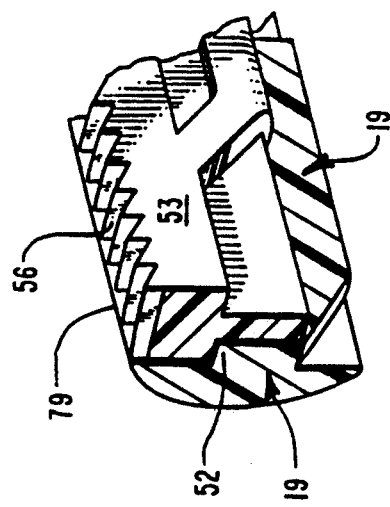
FIG. 7
FIG. 8

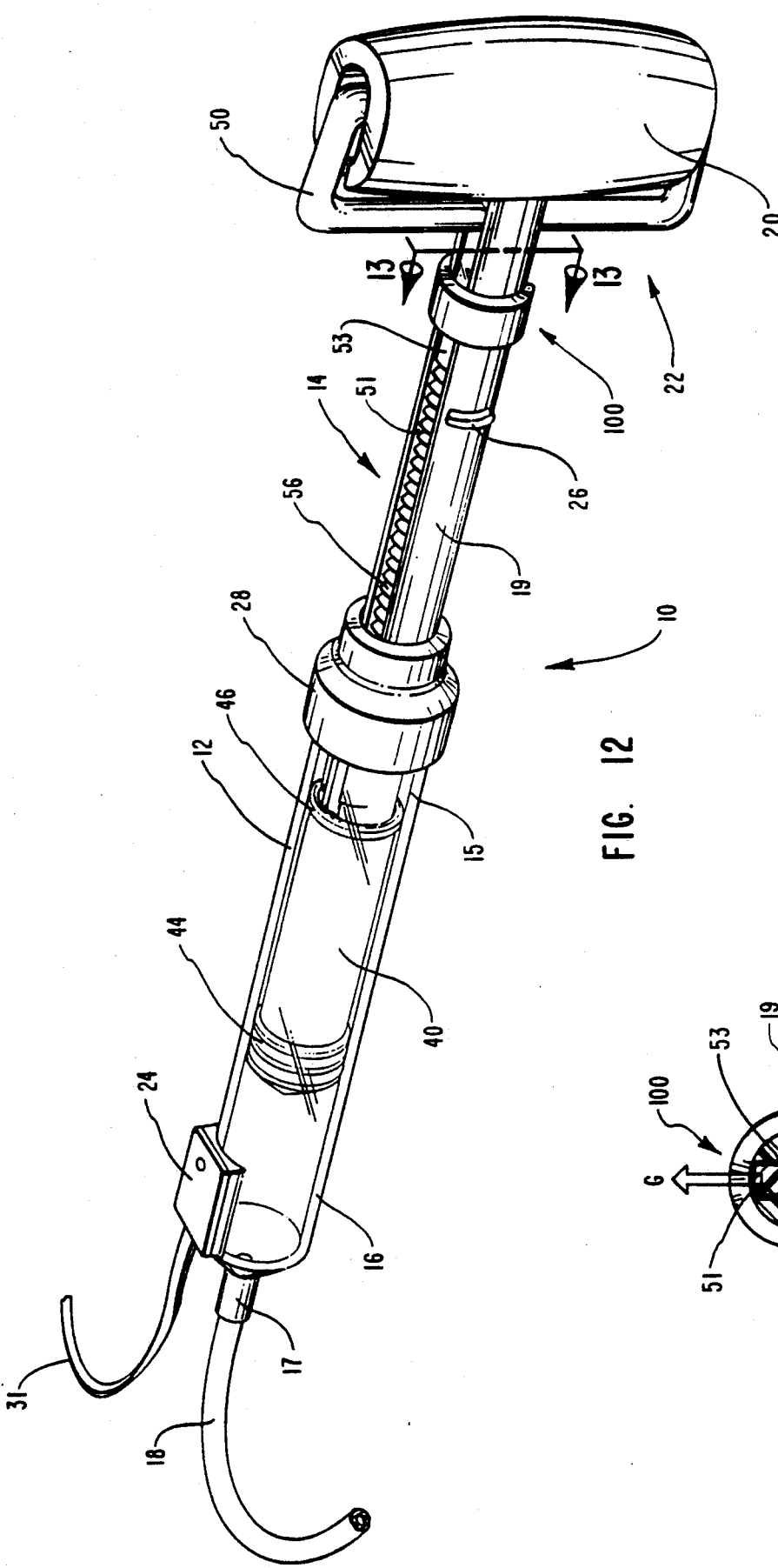
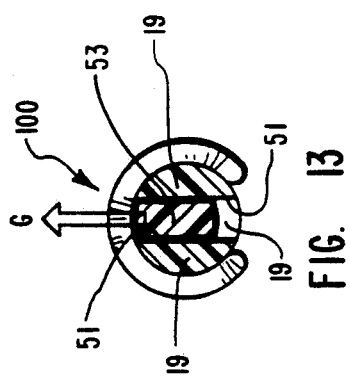
FIG. 12
FIG. 13

LOCKING SYRINGE WITH THREAD-RELEASE LOCK

RELATED APPLICATIONS

This is a continuation-in-part application of U.S. Patent application Ser. No. 434,461 filed Nov. 13, 1989, now U.S. Pat. No. 5,047,015 which was a continuation-in-part application of U.S. patent application Ser. No. 325,561 filed Mar. 17, 1989 now U.S. Pat. No. 5,057,078 both entitled "Locking Syringe," and both naming Gerald L. Foot, Darla R. Gill, Fred P. Lampropoulos, and William Padilla.

BACKGROUND

1. Field of the Invention

The present invention relates to syringes which are capable of operating selectively in either a freely reciprocating mode or a restricted, threaded mode. More particularly, the present invention relates to a locking syringe that incorporates on the plunger thereof a triggering device which may be actuated to retract threads on the plunger, thereby to enable the plunger to move with respect to the barrel in a freely reciprocating rather than in the restricted, threaded mode. The invention has ready application to the field of angioplasty.

2. The Background of the Invention

One of the most basic of the tools used by the medical practitioner is the syringe. Perhaps best known as an instrument used with a needle to inject medicine into a patient, the syringe has also been found useful in a variety of other applications. For example, syringes are particularly useful in performing angiographic procedures.

Angioplasty is a procedure for reducing the blockage which may occur in blood vessels. Over time, blood vessels may become partially or totally blocked due to buildup of cholesterol plaque along the walls of the vessel.

One location where plaque buildup is particularly dangerous is within the coronary arteries. The coronary arteries are those arteries which supply oxygen-rich blood to the heart. Buildup of plaque within the coronary arteries, a condition commonly referred to as coronary artery disease, can cause serious chest pain—angina—and, if not treated, may eventually cause heart failure.

Coronary angioplasty involves opening these blocked coronary arteries by inserting a balloon-tipped catheter into the artery. The balloon is inserted by making an incision usually in the groin or arm. A catheter is then inserted in a blood vessel exposed by the incision and threaded into the coronary artery.

An x-ray sensitive dye is injected into the coronary artery to enable the clinician to accurately position the catheter in the blocked portion of the artery. The catheter is inserted along the artery until the section of the catheter on which the balloon is located is positioned along the blocked portion of the artery.

A fluid is injected into the catheter to inflate the balloon. As the balloon is inflated, the plaque is compressed thereby expanding the narrowed artery. The clinician then withdraws the fluid from the balloon catheter, causing the balloon to deflate. The balloon catheter may then be removed from the patient.

It has been found that a syringe provides an effective tool for the introduction of fluid into the balloon catheter. As the pressure within the balloon must be carefully controlled during the angioplasty procedure, typical syringes having a plunger which may be freely depressed into the barrel are inadequate for this application.

If the pressure within the balloon is too great, the balloon may burst, a circumstance which usually requires immediate emergency surgery to correct. Some prior art attempts at designing a syringe which provides greater control over the pressures achieved in the balloon include providing a syringe which incorporates a plunger which is threadably connected to the barrel. Thus, the plunger may be slowly threaded into the barrel, resulting in a more controlled introduction of fluid into the balloon catheter.

A serious disadvantage to such syringes is the inability to freely and rapidly move the plunger in and out of the barrel in sliding reciprocation. For example, a preferred method of deflating the balloon is to rapidly withdraw the plunger from the barrel to create a negative pressure, thereby causing the fluid to exit the balloon in an attempt to equilibrate the pressure within the balloon catheter. Withdrawing the plunger gradually from the barrel of the syringe by "unscrewing" the plunger requires a great amount of time and, more significantly, results in reduced effectiveness in deflating the balloon.

In recognition of the desirability of a syringe capable of operating in both a freely reciprocating mode and a restricted, threaded mode, syringes have been developed which employ a threaded engagement mechanism on the barrel of the syringe which can be actuated to selectively engage with and disengage from threads on the plunger.

When the thread engagement mechanism is engaged, the syringe is in its restricted threaded mode, so that free reciprocating movement of the plunger sliding within the barrel is prevented. In this restricted mode of operation, the plunger may only be moved within the barrel by its rotation, which gradually moves it into or out of the barrel.

In many syringes employing a thread engagement mechanism on the barrel, the syringe is awkward to use. When using the syringe, the operator must grasp the barrel with one hand and depress the plunger with the other hand, taking care to steadily hold the syringe as the plunger is depressed. Depending on the location and direction of actuation of the thread engagement mechanism, it can be difficult to maintain the syringe in a steady position and control the thread engagement mechanism at the same time.

An additional disadvantage to such syringes is that some prior art syringes require that the barrel of the syringe be aligned in a certain orientation before the thread engagement mechanism can be actuated. This makes the syringe more difficult to use because the user must first ensure that the syringe is properly aligned before actuating the thread engagement mechanism.

A potentially serious flaw exists in known syringe designs incorporating thread engagement mechanisms. When such mechanisms are deactivated, the action of doing so causes corresponding longitudinal movement of the plunger. Such movement is unwanted, as causing potentially dangerous increases or decreases in the pressure within the balloon being inflated by the syringe.

If the balloon were to be expanded beyond acceptable limits, the coronary artery being repaired might be expanded beyond its capacity to yield. Rupture of the coronary artery would require immediate emergency surgery to correct, and, depending on the severity of the rupture, might require immediate bypass surgery.

Many prior art syringes also suffer from the disadvantage that it is impossible to view the fluid within the syringe along its entire path into the balloon catheter. During angioplasty, it is important to prevent air bubbles from entering the balloon catheter. If an air bubble were to enter the balloon and the balloon were to burst, the resulting embolism could cause serious injury to the heart and possibly result in death.

Toward this end, prior devices have relied upon priming of the locking syringe. Priming is accomplished first by placing the output end of the barrel in an elevated position. Hopefully this permits air bubbles in the fluid contents of the barrel to migrate to the output end. This process is frequently encouraged by medical personnel through shaking the syringe or tapping it with other pieces of operating room equipment. After a reasonable amount of time, the output end of the syringe is vented, and the plunger of the device is advanced into the barrel. Any entrapped air bubbles, hopefully then having moved to the output end of the syringe, are expelled with fluid through the vented end of the barrel. If successful, the remaining fluid contents of the barrel are free of air bubbles.

Nevertheless, several problems in relation to this procedure have been observed with known locking syringes. The first and most obvious of these is that of being unable to verify in any direct way that all gas bubbles have been removed from the fluid contents of the syringe.

Secondly, in the case of locking syringes normally biased into a restricted, threaded mode of operation, it has been necessary for personnel working with the syringe to simultaneously activate whatever mechanism is provided in the locking syringe to release it from its restricted, threaded mode of operation and at the same time to manipulate a syringe barrel as described above toward the end of isolating gas bubbles at the output end. Conducting these two tasks simultaneously has presented quite a challenge and has undercut the effectiveness of medical personnel in achieving the objective desired.

Apart from angioplasty, other medical applications would also benefit from a properly designed locking syringe. For example, such a syringe could be advantageously employed in a biopsy procedure to remove tissue or cell samples from a patient for later testing and laboratory examination.

In a biopsy procedure of the type contemplated, a needle is attached to the locking syringe and inserted into the body of the patient such that the end of the needle contacts the tissue desired to be sampled. The plunger is disengaged from its restricted, threaded mode of operation and rapidly withdrawn in the barrel of the syringe, creating a negative pressure within the barrel of the syringe and in the biopsy needle. The negative pressure draws sample tissue into the needle. Utilizing a locking syringe would enable the clinician to lock the plunger in this retracted position and preserves the negative pressure during withdrawal of the needle from the body of the patient.

Nevertheless, many of the problems and disadvantages discussed above with respect to angioplasty syringes also exist in syringes used for biopsy.

BRIEF SUMMARY AND OBJECTS OF THE INVENTION

One object of the present invention is to provide a syringe which affords the operator the capability of selectively operating the syringe in a freely reciprocating mode or, to maintain precise control over the amount of pressure exerted by the syringe, in a restricted, threaded mode.

An additional object of the present invention is to provide a locking syringe by which selective operation in both the freely reciprocating mode and the restricted, threaded mode can be accomplished using the same hand as actuates the plunger.

It is also an object of the present invention to provide a locking syringe as described which incorporates on the plunger of the syringe a triggering mechanism for releasing the syringe from its restricted, threaded mode.

Yet another object of the present invention is a locking syringe which may be selectively operated between the locked and free positions, regardless of the orientation of the barrel of the syringe.

Still another object of the present invention is to provide such a locking syringe which incorporates a triggering device which may be actuated to convert the syringe from its restricted, threaded mode to its freely reciprocating mode, without resulting in any significant reciprocating movement of the plunger with respect to the barrel.

Another object of the present invention is to provide such a locking syringe for which the complete removal o air bubbles from the fluid contents thereof can be directly verified by an operator.

Yet another object of the present invention is a locking syringe as described above in which the triggering device for converting the syringe from its restricted, threaded mode to its freely reciprocating mode can be maintained in a position to permit further manipulation of the syringe in its freely reciprocating mode without the need for the operator to continue to activate the triggering device.

One object of the present invention is, accordingly, to provide a locking syringe which can be easily and reliably primed by freeing the fluid contents thereof of all trapped air bubbles.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a locking syringe is provided that comprises a novel plunger and barrel which together allow the syringe to be selectively operated between a freely reciprocating mode, in which the plunger may slide freely within the barrel in a reciprocating manner, and a restricted, threaded mode, in which the reciprocating movement of the plunger is restricted by placing the plunger in threaded engagement with the barrel. In the locked or engaged position, the plunger may be screwed into or out of the barrel by rotating the plunger, thereby resulting in controlled and gradual reciprocating movement of the plunger relative to the barrel. Additionally, if no force is applied to the plunger to cause it to rotate, the plunger remains locked against any movement of the plunger with respect to the barrel. Thus, one operating the syringe in the locked or restricted mode can maintain precise control over the amount of pressure exerted by the syringe.

Accordingly, a locking syringe is provided comprising a barrel and a plunger at least partially disposed in the barrel so as to engage its interior and be capable of reciprocating sliding movement therein. In one aspect of the present invention, a plunger position maintenance means is provided for selectively restricting reciprocating sliding movement of the plunger in order to hold a plunger in a selected position against a predetermined pressure created within the barrel. Such a plunger position maintenance means itself comprises an internal restricting means and an external restricting means. The internal restricting means is located on a portion of the interior of the barrel. The external restricting means is located along at least a portion of the longitudinal axis of the plunger and is capable of being moved between an engaged position and a disengaged position. In the engaged position, the external restricting means engages the internal restricting means to preclude reciprocating sliding movement of the plunger. In the disengaged position, the external restricting means is freely internal restricting means, so that the plunger is capable of reciprocating sliding movement.

In another aspect of the invention, a trigger means is provided for selectively moving the external restricting means between its engaged and its disengaged position. The trigger means is capable of assuming a first position in which the external restricting means is placed in its engaged position and a second position in which the external restricting means is placed in its disengaged position. In one embodiment of the present invention, the trigger means comprises a handle rigidly secured to the plunger, and a retraction bar rigidly secured to the external restricting means. The retraction bar is selectively movable in relation to the handle between first and second positions which correspond respectively to the first and second positions of the trigger means itself. A retraction bar bias means is included for urging the restriction bar into its first position.

The present invention additionally comprises a locking means for preventing movement of the trigger means into its first position. In this manner, the external restricting means is maintained in its disengaged position in order to permit reciprocating sliding movement of the plunger without the continued need to activate the trigger means of the device. This feature in particular is intended to facilitate priming of the locking syringe.

In one embodiment of the looking means of the present invention, a pawl is secured on one of either the handle or the retraction bar. In the second position of the retraction bar, the pawl is capable of being moved selectively into a locked position which engages the other of the handle or the retraction bar. In the locked position, the pawl prevents the return of the retraction bar into its first position and, accordingly, the return of the external restricting means into its engaged position in which reciprocating sliding movement of the plunger is precluded.

The pawl is secured on the retraction bar, while a pawl receiving aperture is formed in the handle. The locked position of the pawl is achieved by first activating the trigger means of the device and then entering the free end of the pawl into the pawl receiving aperture. The pawl may be provided with resilient legs so as to be removably securable to the retraction bar.

Alternatively, in another embodiment of the locking means, a plug is insertable into an aperture in the handle which is occupied by the retraction bar in the first position thereof. When thusly inserted, the plug prevents movement of the retraction bar into that first position.

The barrel and tip of the syringe are preferably made of a transparent material. Thus, the operator of the syringe may visually verify whether air bubbles are located within the liquid being injected with the syringe, thereby facilitating the priming thereof.

As the syringe incorporates a triggering device which is actuated by a trigger located on the plunger, a clinician is permitted to easily operate the trigger to actuate the triggering device using the same hand with which the plunger is actuated to operate the syringe. This can be accomplished regardless of whether the locking syringe is maintained in the free position or in the locked position.

In a preferred embodiment of the invention, the triggering device is incorporated into the neck of the plunger and includes threads and a series of channels disposed along a spine. Ramps corresponding to each channel are located along an elongated groove in the neck of the plunger such that the spine rests in the groove and each ramp is at least partially disposed within its corresponding channel. Upon actuation of the triggering device, the channels travel along the ramps, causing the spine and thereby the threaded portion of the triggering device to be retracted from engagement with corresponding threads on the barrel. In this retracted position, the spine is fully retracted into the groove in the neck of the plunger and the plunger may freely reciprocate slidably within the barrel.

Under such circumstances, yet another embodiment of a locking means usable with the present invention comprises a resilient clamp selectively attachable about the neck of the plunger during activation of the triggering device in order to maintain the spine fully retracted into the groove therein.

Advantageously, the ramps and channels are disposed at an acute angle with respect to the longitudinal axis of the barrel which is less than or equal to the angle of disposition of the teeth on the threads with respect to the longitudinal axis of the barrel. Thus, as the triggering device is actuated and the channels slide along the ramps, the threads on the triggering device are retracted from the threads on the barrel without any net force resulting which would cause movement of the plunger with respect to the barrel.

When the syringe is designed for angioplasty, it may also be provided with an integral transducer means for measuring the amount of pressure exerted on fluid being injected by the syringe, as more particularly described in copending U.S. patent application Ser. No. 324,938, which is incorporated herein by specific reference.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 7 is a cross sectional view of the pieces of the handle and triggering device illustrated in FIG. 6 showing the spine of the triggering device in a fully retracted FIG. 8 is a cut-away cross-sectional view of the pieces of the handle and triggering device in FIG. 7 taken along section line 8—8 shown therein, illustrating the intermeshing of channels and ramps of that triggering device;

FIG. 12 is a perspective view of a locking syringe incorporating teachings of the present invention, including a second embodiment of a lock for the thread-release mechanism thereof; and FIG. 13 is a transverse, cross-sectional view of the locking syringe of FIG. 12 taken along section line 13—13 therein.

DETAILED DESCRIPTION OF THE PREFERRED EMBODIMENTS

Figure 1:
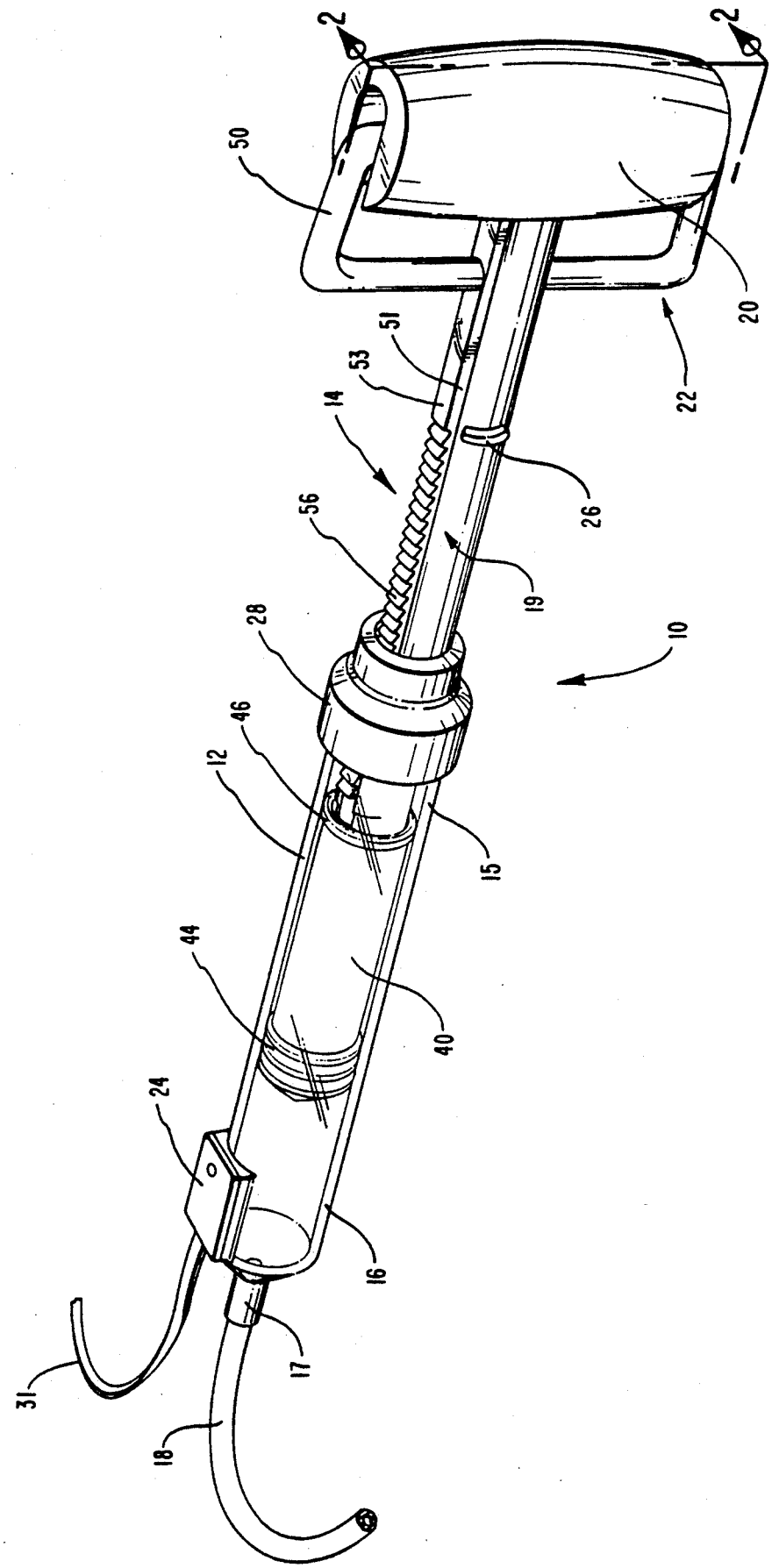
FIG. 1 is a perspective view of a first embodiment of a locking syringe incorporating teachings of the present invention.

Throughout the drawings, like parts are designated with like numerals. In FIG. 1, a first embodiment of a locking syringe 10 is illustrated embodying teaching of present invention. Locking syringe 10 includes a barrel 12 and a plunger 14. The barrel 12 has a plunger insertion end 15 and an output end 16 which is equipped with a tip 17.

A piece of tubing 18 may be attached to the tip 17. Tubing 18 may be connected to a rotatable connector, such as a luer connector, and attached to a balloon catheter (not shown) thereby creating a conduit for fluid communication between barrel 12 and the balloon catheter for use in angioplasty. Alternatively, a needle may be attached to locking syringe 10 at tip 17, thereby enabling the syringe to be used for a biopsy application or an application requiring controlled injection. It will be appreciated that there are a variety of applications for the locking syringe of the present invention and, according to the application, an appropriate attachment may be attached to the syringe at tip 17.

In FIG. 1, plunger 14 can be seen to be attached at a neck 19 to a handle 20. Plunger 14 is also configured with a means for triggering the selection of the mode of operation of the syringe, whether it be the freely reciprocating mode or the restricted, threaded mode. The means for triggering such selection utilizes a triggering device 22. As will be explained in greater detail below, triggering device 22 may be actuated to selectively place plunger 14 in threaded engagement with barrel 12 or to enable plunger 14 to freely reciprocate slidably within barrel 12.

Figure 2:
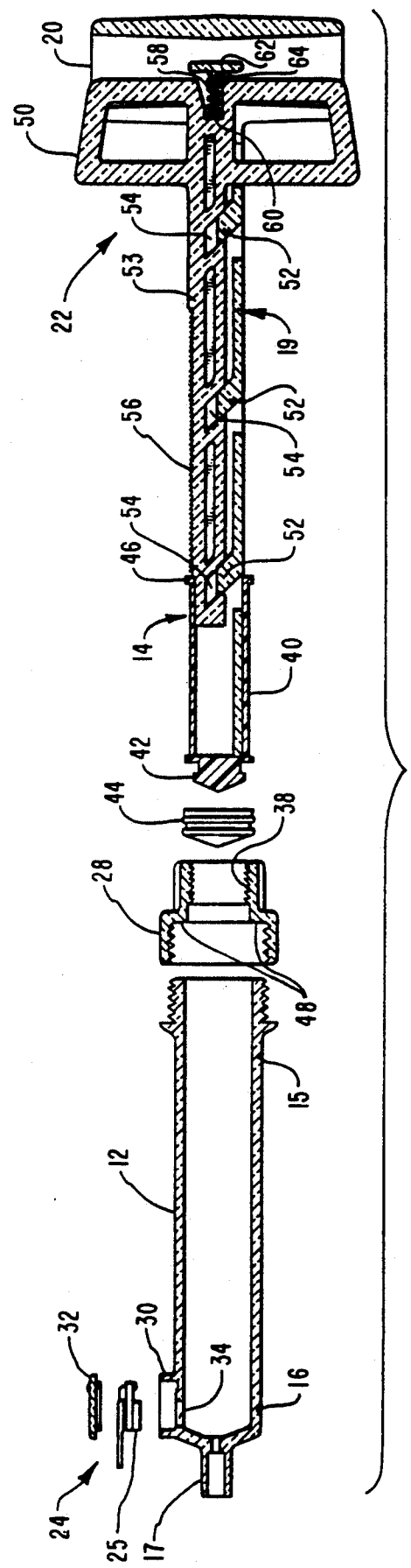
FIG. 2 is an exploded, cross-section view of the components of the locking syringe of FIG. 1 taken along section line 2—2 therein.

With reference in addition to FIG. 2, barrel 12 is seen to further includes a cap 28 which is threadably connected to output end 16 thereof. Cap 28 is provided to facilitate assembly of locking syringe 10. Cap 28 also includes internal restricting means such as helical internal threads 38 which are capable of engaging corresponding threads on plunger 14.

Plunger 14 is configured with a collar 40 having a bulb adaptor 42 at one end. The function and configuration of collar 40 is set forth in greater detail in copending U.S. patent application Ser. No. 173,447, filed Mar. 25, 1988, entitled "Disposable Control Syringe." A rubber bulb 44, such as those known in the art, is attached to bulb adaptor 42.

In operation, collar 40 of the plunger 14 remains disposed within barrel 12. Means are provided on plunger 14 to retain collar 40 within barrel 12. It is presently preferred that a flange 46 be configured on the end of collar 40 for this purpose. As plunger 14 is slidably extracted from barrel 12, flange 46 will engage and abut against a lip 48 of cap 28 to prevent further extraction of plunger 14.

Figure 3:
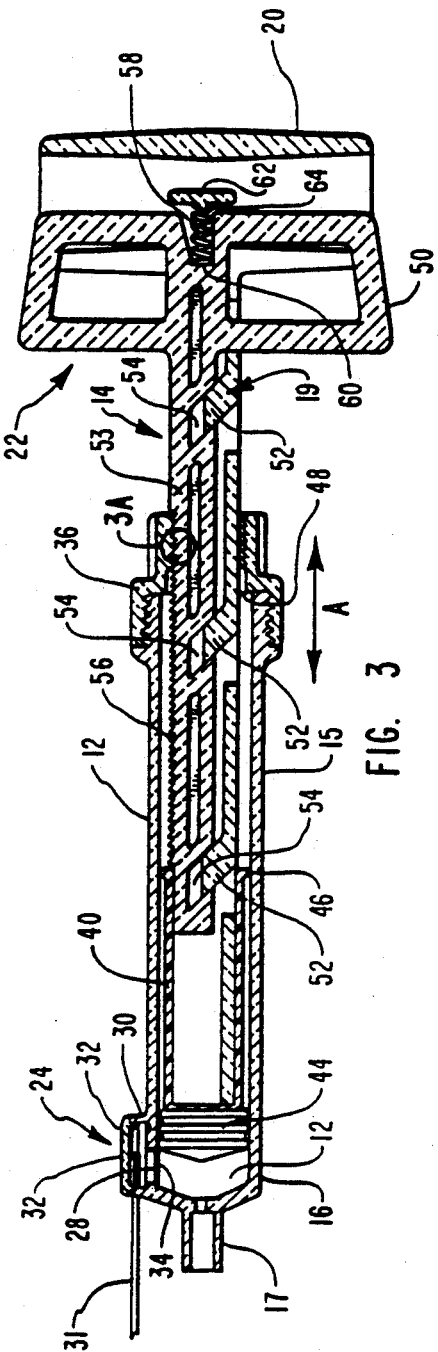
FIG. 3 is a longitudinal, cross-section view of the locking syringe of FIG. 1 in the restricted, threaded mode of operation.

Barrel 12 of the locking syringe 10 further includes a transducer 24 in fluid communication with the interior of barrel 12 for measuring the fluid pressure within barrel 12. In the presently preferred embodiment, the transducer 24 is located at output end 16 of barrel 12, near tip 17, as illustrated in FIGS. 1-3.

In order to effectively measure the pressure within barrel 12, transducer 24 is ideally always in fluid contact, directly or indirectly, with the fluid in the interior of barrel 12. To prevent plunger 14 from being inserted into barrel 12 and blocking the fluid contact between transducer means 24 and barrel 12, a stop 26 shown in FIG. 1 is configured on plunger 14.

Stop 26 acts to prevent plunger 14 from being inserted into barrel 12 beyond the location of stop 26. It will be appreciated that a variety of other means may be employed for preventing plunger 14 from blocking fluid contact between transducer 24 and the fluid in the interior of barrel 12. For example, a ridge could be provided along the interior of barrel 12 adjacent transducer 24 toward the same result.

With reference now specifically to FIG. 2, transducer 24 comprises, for example, a piezoresistive semiconductor integrated circuit chip 25 which mounts within a housing 30 integrally configured on output end 16 of barrel 12. Transducer chip 25 and an electrical cable 31 attached thereto are secured in housing 30 with a suitable potting compound. A transducer cover 32 is provided to enclose the entire assembly in housing 30. A small opening 34 permits the fluid contact between transducer chip 25 and the fluid in the interior of barrel 12. Stop 26 serves as a means to prevent plunger 14 from being inserted into barrel 12 to a point at which bulb 44 would block opening 34.

It can also be seen in FIG. 2, triggering device 22 includes a retraction bar 50 in connection with plunger 14. In a presently preferred embodiment, retraction bar 50 is disposed proximate to handle 20 to facilitate actuating retraction bar 50 with the same hand used to grasp handle 20. It will be appreciated that retraction bar 50 may also be disposed at various locations along plunger 14.

Triggering device 22 further includes an extended longitudinal groove 51 having a series of ramps 52 disposed along the walls thereof. A spine 53 having a corresponding channel 54 for each ramp 52 is disposed within groove 51, such that each ramp 52 is disposed in register with and at least partially within a corresponding channel 54 during the operation of locking syringe 10. This relationship is maintained in both the freely reciprocating mode of operation or the restricted, threaded mode.

Although in a presently preferred embodiment of the invention three or four sets of ramps and channels are employed, it will be appreciated that the number of ramps and channels is largely a matter of design choice. It has been found that increasing the number of ramps and channels may lend stability to plunger 14 and prevent unwanted deflection in triggering device 22. Further, although the preferred embodiment has channels 54 disposed on spine 53 and ramps 52 disposed on the walls of groove 51, it should be understood that alternatively these relative positions could be reversed. Then channels 54 would be disposed along the walls of groove 51 in neck 19 and ramps 52 would be disposed along spine 53.

In a preferred embodiment of triggering device 22, external threads 56 are configured along one side of spine 53 of triggering device 22. External threads 56 are so configured as to be capable of threadably engaging internal threads 38 located within cap 28. External threads 56 are noncontinuous, as the tooth pattern thereof does not continue around spine 53 to connect adjacent teeth.

Triggering device 22 is further configured with a means for biasing external threads 56 into threaded engagement with internal threads 38 and a means for biasing retraction bar 50 in a nonactuated position correspondingly. One presently preferred mechanism for accomplishing this function is to employ a spring 58, as illustrated in FIG. 2, which rests between a notch 60 in retraction bar 50 and a post 62 attached to handle 20.

Post 62 includes a nib 64 which fits inside the end of spring 58 resting against post 62. Nib 64 assists in positioning spring 58 against post 62 and preventing spring 58 from sliding laterally along post 62. Thus, post 62 and nib 64 act to properly position retraction bar 50 with respect to handle 20 and to prevent any lateral movement of retraction bar 50 with respect to handle 20.

The operation of the locking syringe 10 may be best explained by reference to FIGS. 3, 3A, and 4. In FIG. 3, locking syringe 10 according to the present invention is illustrated in its restricted, threaded mode of operation. In the restricted mode of operation, plunger 14 is in threaded engagement with barrel 12 by the engagement of external threads 56 with internal threads 38. Due to such threaded engagement, the slidably reciprocating movement of plunger 14 within barrel 12 is restricted. A force applied in the longitudinal direction of handle 20 (substantially in the direction of arrow A shown in FIG. 3) will not result in movement of plunger 14 with respect to barrel 12. Thus, the force of back pressure on the fluid being dispensed by locking syringe 10 will not cause plunger 14 to recede out of barrel 12, nor can any inadvertent excessive compression by plunger 14 be effected.

In the restricted mode of operation, plunger 14 may, however, be moved in and out of barrel 12 by rotating handle 20. Depending on the pitch of threads 56 and 38, plunger 14 will move in a helical path which translates into a predetermined longitudinal distance within barrel 12 with each rotation of handle 20. In this manner, the rotational movement of plunger 14 causes gradual longitudinal movement of rubber bulb 44 within barrel 12. This effects slight pressure differences in the material being injected or extracted by locking syringe 10. In some applications, such as in angioplasty, when locking syringe 10 is used to exert a controlled pressure, the ability to obtain slight longitudinal movements of plunger 14 or to move plunger 14 to a predetermined point of insertion are necessary for obtaining and exactly controlling the desired pressures.

Figure 4:
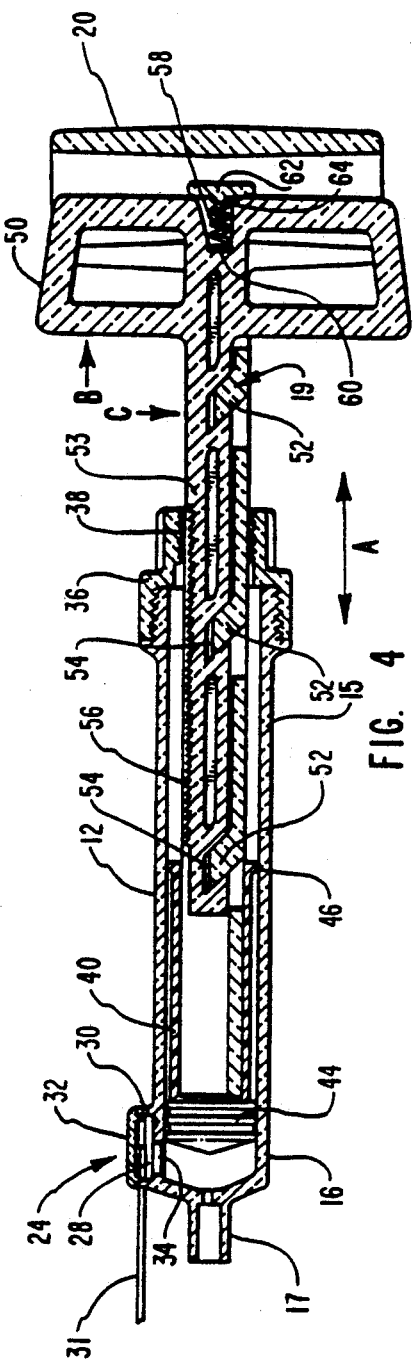
FIG. 4 is a longitudinal, cross-section view of the locking syringe of FIG. 1 in the freely reciprocating mode of operation.

FIG. 4 illustrates the locking syringe 10 of the present invention with triggering device 22 actuated to place locking syringe 10 in freely reciprocating mode of operation. With triggering device 22 so actuated, a longitudinally directed force applied to handle 20 in the manner of arrow A will result in the substantially unrestricted slidable movement of plunger 14 longitudinally within barrel 12. Thus, rapid movement of plunger 14 with respect to barrel 12 may be obtained with locking syringe 10 in the freely reciprocating mode of operation.

Many applications requiring a locking syringe also require that the syringe be capable of operating in such a freely reciprocating mode. For example, when performing angioplasty, it is first necessary to fill the balloon catheter with a liquid before applying pressure on the liquid to expand the balloon within the blocked blood vessel. Initially, filling the balloon catheter can be quickly and easily accomplished with a syringe in such a freely reciprocating mode of operation.

Also, when the angioplasty procedure is completed and it is desired to deflate the balloon, the balloon may be most efficiently and rapidly deflated by creating a negative pressure within locking syringe 10. This acts to extract liquid out of the balloon catheter, thereby deflating the balloon. The creation of negative pressure within locking syringe 10 can be effectively accomplished when locking syringe 10 is in the freely reciprocating mode of operation.

Triggering device 22 is actuated by applying a force on retraction bar 50 in the direction shown in FIG. 4 by arrow B. Unlike prior art type syringes, this may be advantageously done by the clinician with a one-handed squeezing movement using the same hand that moves plunger 14. The clinician grasps handle 20 and, by squeezing retraction bar 50 and handle 20, is able to apply a force on retraction bar 50 in the direction of arrow B and an equal and opposite force on handle 20. In the process, there is no resulting net force on plunger 14 which would tend to move plunger 14 in or out of barrel 12. The force applied to retraction bar 50 acts to compress spring 58 and causes channels 54 to slide over ramps 52, bringing spine 53 into longitudinal groove 51 in a direction indicated in FIG. 4 by arrow C.

Figure 5:
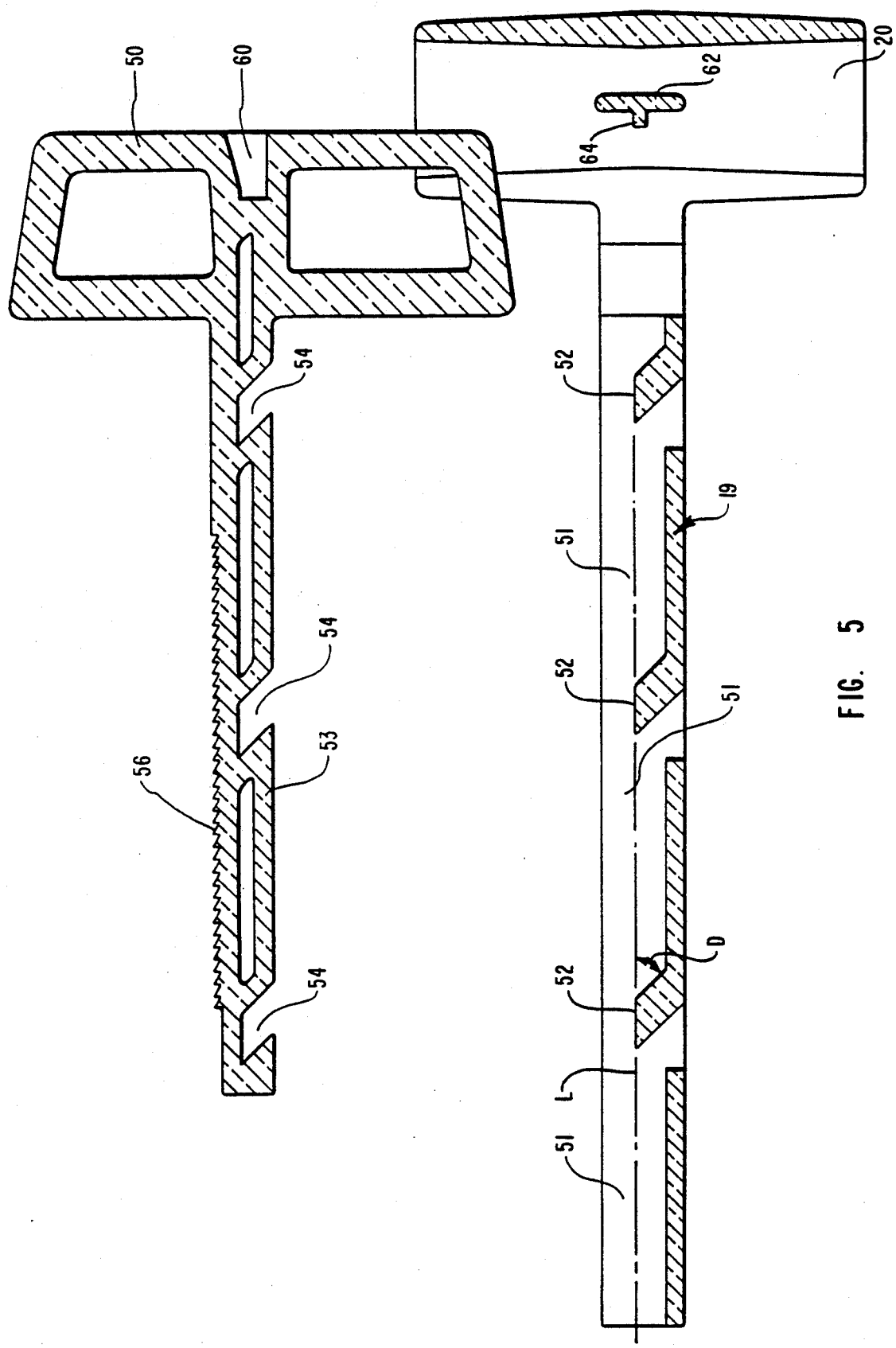
FIG. 5 is a disassembled longitudinal, cross-section view of the pieces of the handle and triggering device of the locking syringe of FIG. 1.

The two primary components triggering device 22 are illustrated in FIG. 5. As seen there neck 19 is connected to handle 20, and spine 53 connected to retraction bar 50 is slidably disposed in longitudinal groove 51 in neck 19. When the components of triggering device 22 shown in FIG. 5 are assembled as illustrated in FIGS. 3 and 4, channels 54 each engage a ramp 52.

As triggering device 22 is actuated by applying a force to retraction bar 50 in the direction of arrow B, spine 53 retracts in the direction in which channels 54 are forced to travel along ramps 52. As channels 54 travel along ramps 52, external threads 56 located on spine 53 are retracted from engagement with internal threads 38.

The direction of travel of external threads 56 in this process is dictated by the angle of disposition D made by ramps 52. For example, a presently preferred angle of disposition of ramps 52 is approximately 45 degrees with respect to longitudinal axis L. Thus, as external threads 56 are retracted upon actuation of triggering device 22, external threads 56 move both longitudinally in the direction of arrow B shown in FIG. 4 and laterally in the direction of arrow C shown in that same figure.

In some applications of a syringe according to the present invention, it is preferred that triggering device 22 be actuatable to change operating mode of the locking syringe between the restricted, threaded mode of operation to the freely reciprocating mode, without causing perceptible resulting movement of plunger 14 longitudinally with respect to barrel 12. Movement of plunger 14 with respect to barrel 12 may be avoided as external threads 56 are retracted from engagement with internal threads 38, if the angle of disposition of the external and internal threads is greater than or equal to the angle of disposition of ramps 52 and channels 54. Under such conditions the direction of movement of spine 53 in longitudinal groove 51 is at an angle that will not cause the threads to bind against each other.

Figure 3A:
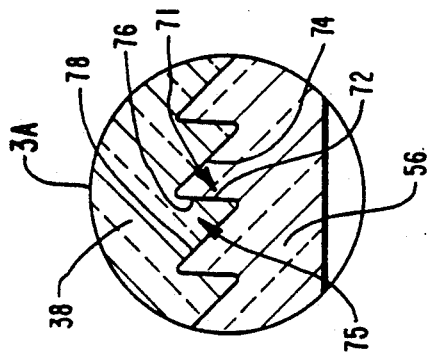
FIG. 3A is an enlarged detail sectional view of a portion of the internal and external threads illustrated in FIG. 3.

FIG. 3A is an enlarged view of the internal and external threads 38 and 56 of FIG. 3 that illustrates the non-symmetrical form of the teeth in internal threads 38 and external threads 56. As can be observed in FIG. 3A, each tooth 71 of the external threads 56 has a leading edge 72 and a trailing edge 74. Each tooth 75 of internal threads 38 has a leading edge 76 and a trailing edge 78. Leading edges 72 of teeth 71 of external threads 56 and leading edges 76 of teeth 75 of internal threads 38 are preferably disposed at angles with respect to each other which permit the teeth to mesh properly The same is true of trailing edges 74 of teeth 71 of external threads 56 and trailing edges 78 of teeth 75 of internal threads 38.

In a preferred embodiment, trailing edges 74 and 78 are disposed at substantially the same acute angle with respect to the longitudinal axis L of plunger 14 and barrel 12 shown in FIG. 5 as the acute angle of disposition D associated with ramps 52 and channels 54. Thus, as external threads 56 are moved from the engaged position thereof of the disengaged position thereof, teeth 71 on exterior threads 56 retract without contacting trailing edge 78 of teeth 75 on internal threads 38 which would cause longitudinal movement of plunger 14 in barrel 12. Conversely, as external threads 56 are moved from the disengaged position thereof to the engaged position thereof, minimal longitudinal movement, is imparted to plunger 14 within barrel 12. Significant longitudinal movement would result in a significant change in the pressure being exerted by the locking syringe 10. As noted above, this would not be acceptable for certain applications of a locking syringe.

If slight increases of pressure within barrel 12 of locking syringe 10 can be tolerated as triggering device 22 is actuated, a variety of combinations of angles may be utilized. It has been found that an angle of disposition D reflected in ramp 52 and channels 54, as well as in trailing edges 72 and 78 of teeth 71 and 75, respectively, of approximately 45 degrees is preferable.

Leading edges 72 and 76 of teeth 71 and 75, respectively, are preferably disposed at an angle of approximately two degrees from the normal to longitudinal axis L of plunger 14 and barrel 12. This two-degree draft is primarily to assist in removing the parts from their molds during the manufacturing process when the parts are molded from plastic.

Pressures of up to approximately 20 atmospheres are not uncommon in angioplasty applications of locking syringe 10. In order to prevent plunger 14 from ratcheting back when a substantial back pressure is built up inside barrel 12 of locking syringe 10, ramps 52 are canted towards tip 17 of barrel 12. For other applications, it may be desirable to reverse the cant of ramps 52. For example, when locking syringe 10 is used primarily or exclusively for creating substantial negative pressures, ramps 52 may be canted away from tip 17, to prevent plunger 14 from ratcheting into barrel 12 as substantial negative pressures are developed.

When it is desired to release locking syringe 10 from its freely reciprocating mode of operation and return it to the restricted threaded mode of operation, the force being applied to retraction bar 50 in the direction of arrow B in FIG. 4 is merely released. Under the biasing force of spring 58, spine 53 will then travel up ramps 52 in a direction to take spine 53 out of longitudinal groove 51, returning external threads 56 to a position of threaded engagement with internal threads 38, as illustrated in FIG. 3

With retraction bar 50 attached to plunger 14 of locking syringe 10, triggering device 22 may be actuated regardless of the rotational orientation of handle 20 to barrel 12. To actuate triggering device 22, the operator of locking syringe 10 need only grasp barrel 12 with one hand and hold handle 20 with the other. Retraction bar 50 may then be easily actuated with the hand which is holding handle 20.

Figure 6:
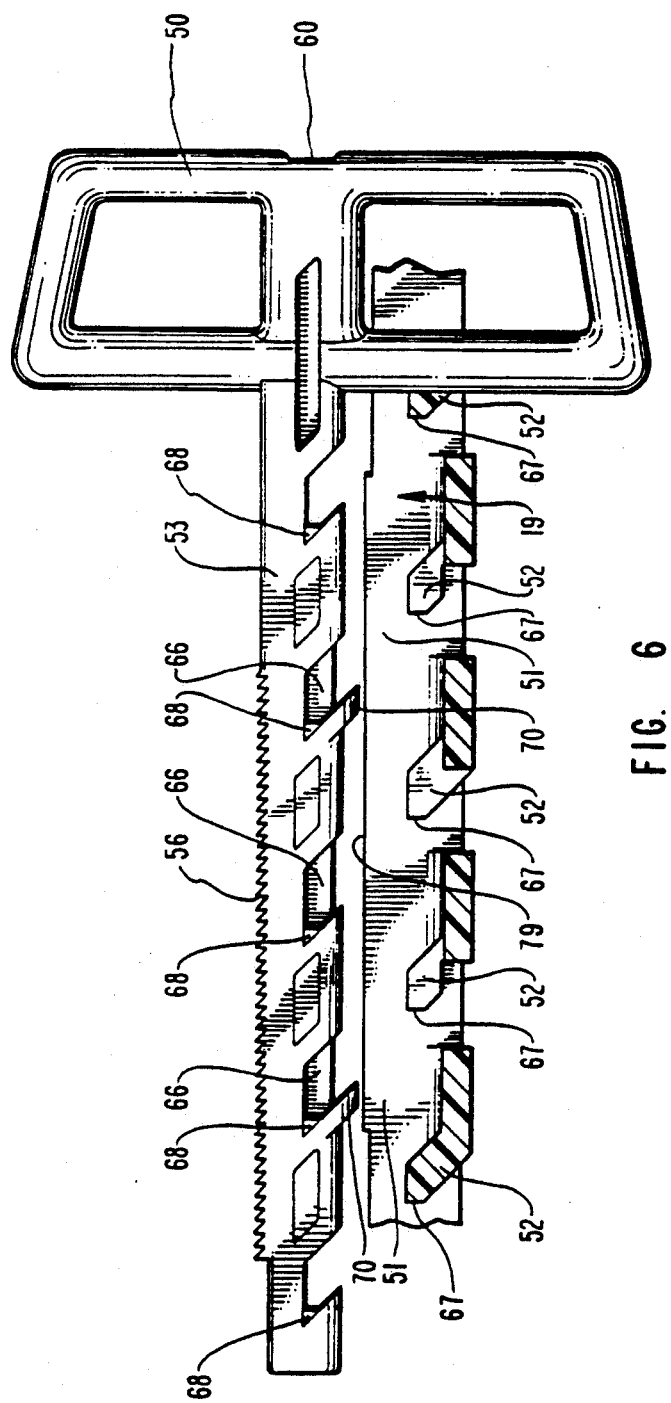
FIG. 6 is a cross-sectional view of the pieces of a second embodiment of the handle and the triggering device of a locking syringe like that of FIG. 1.

In another preferred embodiment of the present invention, shown in FIGS. 6–8, the strength and stability of plunger 14 is enhanced by reducing the amount of empty space within the mechanism of triggering device 22. Wear on external threads 56 may also be reduced by increasing the available travel distance for spine 53 into longitudinal groove 51, so that spine 53 retracts fully into groove 51 when external threads 56 are moved out of the engaged position thereof.

In the embodiment shown in FIGS. 6–8, spine 53 has channels 54 which are arranged in pairs in which each channel 54 of the pair is in lateral register with the other with a support gusset 66 disposed longitudinally and centered along spine 53 between the channels 54 in each pair. Support gussets 66 add rigidity and strength to spine 53. Ramps 52 are provided on each side of longitudinal groove 51 that register with channels 54. To reduce the likelihood that ramps 52 may snag and prevent full retraction of spine 53 into longitudinal groove 51, ramps 52 have a bevelled leading edge 67. Each channel 54 on spine 53 correspondingly has a wedge 68 which compliments bevelled leading edge 67 of each ramp 52 when spine 53 is fully retracted into longitudinal groove 51. Wedges 68 add volume and further stability to spine 53.

Also, at least one protruding arm 70 is provided on spine 53 to assist maintaining orientation of spine 53 within longitudinal groove 51 during movement spine 53 along ramps 52 and to enhance the lateral stability of plunger 14.

FIG. 7 shows spine 53 fully retracted into longitudinal groove 51, so that the tips of external threads 56 do not extend beyond upper edge 79 of neck 19. In this manner, during free sliding reciprocation of plunger 14 within barrel 12 there will be no grinding or undesired racheting of external threads 56 against internal threads 38, which could cause grinding and racheting, wear and breakage to the teeth thereof.

As can be seen in FIG. 8, the preferred embodiment illustrated significantly reduces the amount of empty space within the mechanism of triggering device 22, thereby increasing the strength and stability of plunger 14.

It will be appreciated by one skilled in the relevant art that a syringe according to the present invention may be made of a variety of materials. It is presently preferred, however, that barrel 12, including tip 17, be made of a transparent material, such as a clear plastic. Thus, the operator of the syringe can visually ascertain whether there are any air bubbles in the contents of barrel 12.

Figure 9:
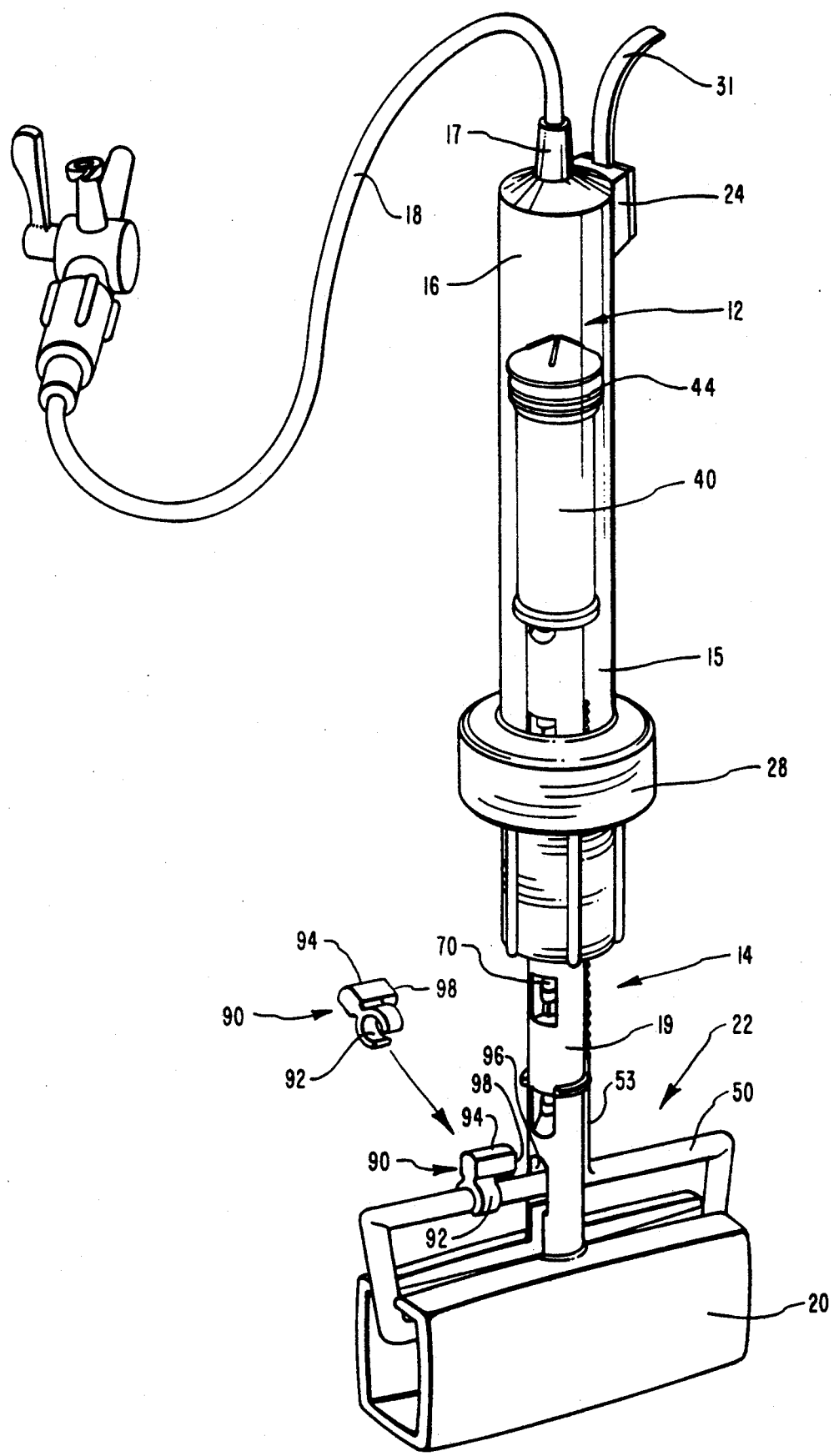
FIG. 9 is a perspective view of a locking syringe incorporating teachings of the present invention, including a first embodiment of a lock for the thread-release mechanism thereof.

FIG. 9 shows locking syringe 10 provided with an additional aspect of the invention intended to facilitate the priming of locking syringe 10 to remove air bubbles from the fluid contents thereof. Locking syringe 10 shown in FIG. 9 includes a barrel 12 and a plunger 14 at least partially disposed therewithin engaging the interior thereof and being capable of reciprocating sliding movement therein.

Locking syringe 10 is provided with a plunger position maintenance means for selectively restrictive sliding movement of plunger 14 to hold plunger 14 in a selected position against the predetermined pressure created within barrel 12. As already disclosed, for example, in relation to FIGS. 3 and 4, a suitable plunger position maintenance means comprises an internal restricting means located on a portion of the interior of barrel 12 and an external restricting means located along at least a portion of the longitudinal axis of plunger 14. The internal restricting means takes the form of internal threads 38 formed on cap 28. The external restricting means comprises external threads 56 located along spine 53 which is attached to retraction bar 50 and slidably disposed in longitudinal groove 51.

Figure 10:
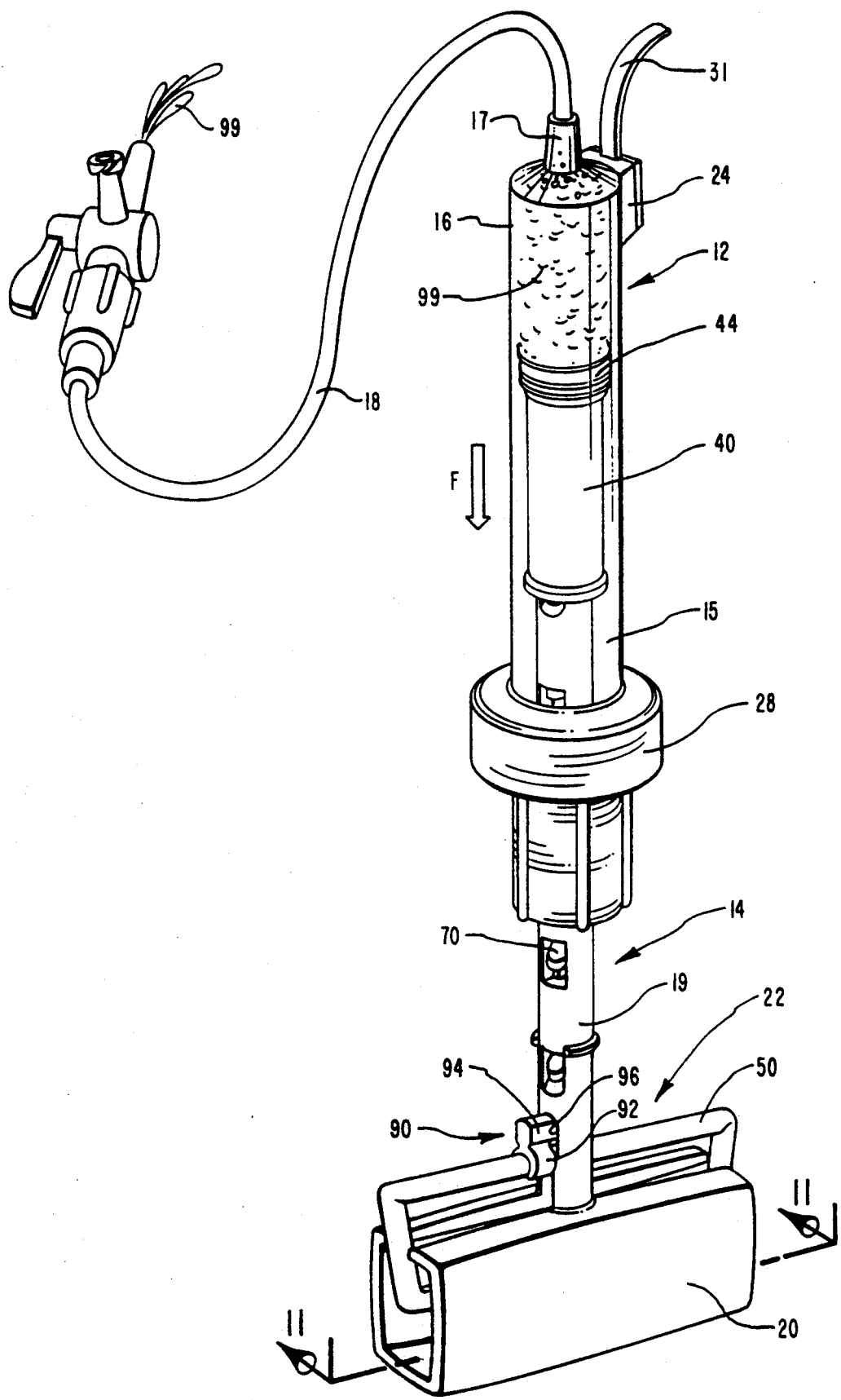
FIG. 10 is a perspective view of the locking syringe of FIG. 9 with the lock for the thread-release mechanism thereof engaged.

As thus configured, external threads 56 are movable between an engaged position illustrated in FIG. 3 and a disengaged position illustrated in FIG. 4. In the engaged position, which is also the position shown in FIG. 9, external threads 56 engage internal threads 58 to restrict reciprocating sliding movement of plunger 14 in barrel 12. In the disengaged position external threads 56 are free of internal threads 38 and plunger 14 is capable of engaging and reciprocating sliding movement in barrel 12. This position is shown in FIG. 10.

According to another aspect of the invention, locking syringe 10 is provided with a trigger means for selectively moving external threads 56 between the engaged and disengaged position thereof. The trigger means of the present invention is capable of assuming a first position in which external threads 56 are placed in the engaged position thereof and a second position in which external threads 56 are placed in the disengaged position thereof. Thus, the first position of the trigger means of the present invention corresponds to the relationship of elements illustrated in FIGS. 3 and 9. Correspondingly, the second position of the trigger means of the present invention corresponds to the relationship of elements illustrated in FIGS. 4 and 10.

As already illustrated by way of example, the trigger means of the present invention comprises a handle 20 rigidly secured to plunger 14 at neck 19. Retraction bar 50 is rigidly secured to spine 53 upon which external threads 56 are disposed. Retraction bar 50 is capable of being selectively moved relative to handle 20 between first and second positions which correspond respectively to the first and second positions of the trigger means of the invention. Spring 58 shown in FIG. 3 functions as a retraction bar bias means for urging retraction bar 50 into the first position thereof, wherein reciprocating sliding movement of plunger 14 is possible.

According to another aspect of the present invention, locking syringe 10 includes a locking means for preventing movement of the trigger means into the first position thereof, thereby to maintain external threads 56 in the disengaged position thereof and to permit reciprocating sliding movement of plunger 14. The locking means thereby relieves an operator of locking syringe 10 from needing to continue to pull retraction bar 50 toward handle 20 and overcome the effect of spring 58. The locking means thus facilitates priming of locking syringe 10 by permitting its operation in the freely reciprocating mode without continuing to hold the trigger means of the invention in its first position.

FIG. 9 illustrates one embodiment of a locking means configured according to present invention. There, as shown by way of example and not limitation, a pawl 90 is removably securable to retraction bar 50 by a pair of resilient legs 92 which snap about retraction bar 50. When thusly secured to retraction bar 50, pawl 90 is pivotable thereabout and longitudinally slidable toward and away from neck 19.

It is the purpose of pawl 90 to prevent retraction bar 50 from returning to the first position thereof illustrated in FIG. 9 once retraction bar 50 is moved into the second position thereof by being drawn longitudinally toward handle 20 in the manner illustrated in FIG. 10.

Thereupon, the free end 94 of pawl 90 can through a combination of longitudinal movement on and pivoting about retraction bar 50 be entered into a pawl receiving aperture 96 formed in neck 19. Thus, when retraction bar 50 is in the second position thereof, pawl 90 can be moved selectively into a locked position engaging handle 20 and preventing movement of retraction bar 50 out of the second position thereof in which free longitudinal movement of plunger 14 is possible.

Figure 11:
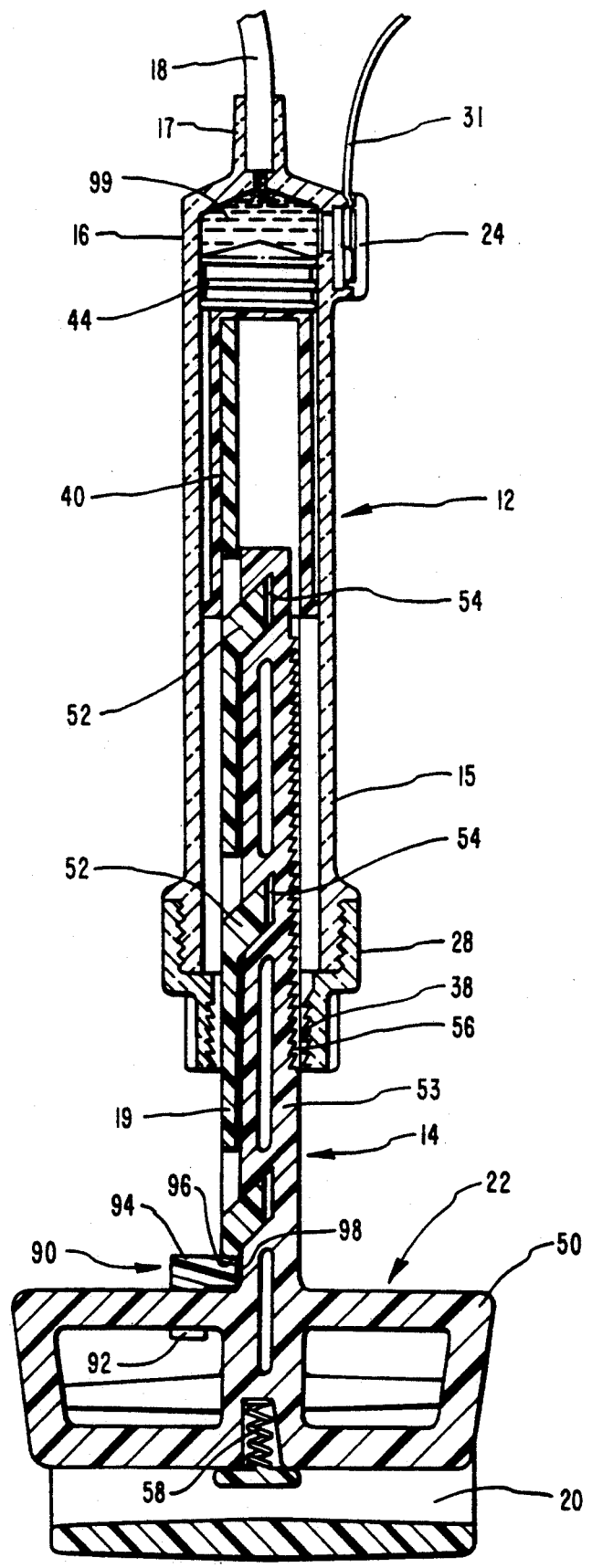
FIG. 11 is a longitudinal, cross-sectional view of the locking syringe of FIG. 10 taken along section line 11—11 therein.

The action of pawl 90 in effecting this result is more clearly appreciated by reference to the cross-section in FIG. 11. There it can be seen that pawl 90 functions as a wedge and preventing retraction bar 50 attached to spine 53 with external threads 56 thereon from returning under the influence of spring 58 into a position in which external threads 56 engage internal threads 38. Thus, the operator of locking syringe 10 may release the compressive forces exerted thereby between traction bar 50 and handle 20 without having external threads 56 engage internal threads 38. The stub 98 at free end 94 of pawl 90 serves to fill pawl receiving aperture 96 which is occupied by retraction bar 50 in the first position thereof. This precludes any return movement of retraction handle 50 thereinto.

Thus, actuation of the locking means of the present invention permits retraction bar 50 to be released, while locking syringe 10 remains in the freely reciprocating mode of operator. This frees both hands of the operator for the purpose of priming the fluid contents of locking syringe 10 to remove air bubbles therefrom. One method for doing so involves orienting locking syringe 10 with output end 16 of barrel 12 in an upright position as shown in FIG. 10. This enables bubbles in the fluid contents 99 of barrel 12 to migrate toward tip 17. Barrel 12 is preferably comprised of a transparent material to enable visual verification of this process.

With locking syringe 10 in the vertical position illustrated in FIG. 10, the operator grasps barrel 12 and exerts a force thereon in the direction indicated by arrow F in FIG. 10. This has the effect of urging plunger 14 into barrel 12, whereupon fluid contents 99 from output end 16 of barrel 12 are forced therefrom through tubing 18 carrying therewith all entrapped air bubbles. Once this process is completed, the reapplication of compressive forces between retraction bar 50 and handle 20 will permit the removal of pawl 90 from pawl receiving aperture 96. If desired, pawl 90 may be removed entirely from retraction handle 50. At this point, with locking syringe 10 primed, pawl 90 can be discarded.

Naturally, the relative positions of pawl 90 and pawl receiving aperture 96 could be reversed. A structure such as pawl 90 could be selectively or permanently secured to neck 19 in a manner so as to be pivotable into a position that would engage and wedge retraction bar 50 in the second position thereof. This would also prevent movement of retraction bar 50 into the first position thereof shown in FIG. 9 and keep locking syringe 10 in its freely reciprocating mode of operation.

Additionally, an operator of locking syringe 10 may choose only to employ stub 98 of pawl 90 without attaching pawl 90 to retraction bar 50. Under such circumstances, only the effect of stub 98 in filling pawl receiving aperture 96 would be employed. With retraction arm 50 drawn into the second position thereof illustrated in FIG. 10, stub 98 at free end 94 of pawl 90 would be inserted into pawl receiving aperture. This would fill pawl receiving aperture 96, preventing movement of retraction arm 50 into the first position thereof in which retraction arm 50 occupies pawl receiving aperture 96. Thus, stub 98 at free end 94 of pawl 90 could be utilized without recourse to resilient legs 92.

Yet another embodiment of a locking means according to the present invention is shown in relation to locking syringe 10 illustrated in FIG. 12. There, retraction arm 50 is in the second position thereof in which spine 53 bearing external threads 56 is laterally withdrawn into longitudinal groove 51 in neck 19. In the position shown, plunger 14 is capable of reciprocating movement within barrel 12. In order to retain retraction bar 50 and handle 20 in the relative position illustrated, a second embodiment of a locking means according to the present invention could be utilized.

As shown by way of example a resilient C-shaped clamp 100 is snapped about neck 19 traversing longitudinal groove 51. Clamp 100 serves to prevent spine 53 from moving laterally out of longitudinal groove 50. In this manner all movement of spine 53 is simultaneously prevented, including that which with retraction bar 50 attached thereto would permit external threads 56 to engage internal threads 38 in the manner illustrated in FIG. 3. The effect of clamp 100 in this regard is more fully understood by reference to FIG. 13.

The effect of spring 58 shown in FIG. 11 between handle 20 and retraction bar 50 is to urge retraction bar 50 and spine 53 attached thereto in a direction toward barrel 12. In the process, due to the interaction of clamps 52 and channels 54, shown for example in FIG. 11, spine 53 is simultaneously directed radially out of longitudinal groove 51 in the upward direction as shown in FIG. 13 by arrow G. Nevertheless, with clamp 100 traversing the opening to slot 51 in the direction of arrow G, spine 53 can engage in no lateral movement, and accordingly longitudinal movement thereof with retraction bar 50 is also precluded. Under such circumstances, priming of the fluid contents of locking syringe 10 can be undertaken in the manner described relative to FIG. 10. Thereafter clamp 10 may be removed from neck 10 24 and either retained or discarded.

Thus it can be seen that according to the teachings of the present invention a locking syringe is provided in which the thread-release mechanism thereof can be temporarily locked out to permit an operator to use both hands for the purpose of removing air bubbles from the fluid contents of the syringe. When the threads are thusly locked out of engagement with each other, freely reciprocating movement of the plunger in the barrel of the syringe is possible. The locking means of the present invention permits this state to be maintained without continued activation of the thread release mechanism itself. Several embodiments of structures for effecting the lock of the thread release mechanism have been disclosed, including a pivotable pawl removably attachable to the retraction bar of the thread release mechanism and a resilient clamp securable about the neck between the handle and the plunger.

It will be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A locking syringe for maintaining therewithin a predetermined pressure created by relative movement of components of the syringe, the locking syringe comprising:

(a) a barrel;

(b) a plunger at least partially disposed within said barrel engaging the interior thereof and being capable of reciprocating sliding movement therein;

(c) plunger position maintenance means for selectively restricting reciprocating sliding movement of said plunger to hold said plunger in a selected position against the predetermined pressure created within said barrel, said plunger position maintenance means comprising:

(i) internal restricting means located on a portion of said interior of said barrel; and (ii) external restricting means located along at least a portion of the longitudinal axis of said plunger, said external restricting means being moveable between an engaged position in which said external restricting means engages said internal restricting means to restrict reciprocating sliding movement of said plunger and a disengaged position in which said external restricting means is free of said internal restricting means and said plunger is capable of reciprocating sliding movement, (d) trigger means for selectively retracting said external restricting means between said engaged and said disengaged position thereof, said trigger means being capable of assuming a first position in which said external restricting means is placed in said engaged position thereof and a second position in which said external engagement means is placed in said disengaged position thereof; and (e) locking means for preventing movement of said trigger means into said first position thereof, thereby to maintain said external restricting means in said disengaged position thereof and to permit reciprocating sliding movement of said plunger.

2. A locking syringe as recited in claim 1, further comprising plunger movement bias means for urging said external restricting means into said engaged position thereof.

3. A locking syringe as recited in claim 1, wherein said trigger means comprises:

(a) a handle rigidly secured to said plunger;

(b) a retraction bar rigidly secured to said external restricting means, said retraction bar being selectively moveable relative to said handle between first and second positions corresponding, respectively, to said first and second positions of said trigger means; and (c) retraction bar bias means for urging said retraction bar into said first position thereof.

4. A locking syringe as recited in claim 3, wherein said locking means comprises a pawl secured to one of said handle or said retraction bar, said pawl in said second position of said retraction bar being capable of being moved selectively into a locked position engaging the other of said handle or said retraction bar, said pawl in said locked position thereof preventing movement of said retraction bar out of said second position thereof.

5. A locking syringe as recited in claim 4, wherein said pawl is pivotally mounted to one of said handle or said retraction bar.

6. A locking syringe as recited in claim 5, wherein said locking means further comprises a pawl receiving aperture formed in the other of said handle or said retractor bar, the free end of said pawl being entered into said pawl receiving aperture in said locked position of said pawl.

7. A locking syringe as recited in claim 4, wherein said pawl is removable secured to one of said handle or said retraction bar.

8. A locking syringe as recited in claim 7, wherein said pawl is removably secured to said retraction bar.

9. A locking syringe as recited in claim 8, wherein said pawl comprises a pair of resilient legs capable of resiliently clasping said retraction bar.

10. A locking syringe as recited in claim 4, wherein said pawl is pivotally mounted to said retraction bar.

11. A locking syringe as recited in claim 10, wherein said locking means further comprises a pawl receiving aperture formed in said handle, the free end of said pawl being entered into said pawl receiving aperture in said locked position of said pawl.

12. A locking syringe as recited in claim 11, wherein said pawl is longitudinally slidable along said retraction bar.

13. A locking syringe as recited in claim 3, wherein said locking means comprises a plug insertable into an aperture formed in said plunger and occupied by said retraction bar in said first position thereof, said plug when inserted into said aperture preventing movement of said retraction bar into said first position thereof.

14. A locking syringe as recited in claim 13, wherein said plug comprises the free end of a pawl removably securable to said retraction bar.

15. A locking syringe as recited in claim 1, wherein said trigger means is situated relative to said plunger so as to be capable of being actuated without regard to the rotational orientation of said plunger relative to said barrel.

16. A locking syringe as set forth in claim 1, wherein said internal restricting means comprises internal threads located on said interior of said barrel, and said external restricting means comprises external threads located along at least a portion of the longitudinal axis of said plunger, said external threads making threaded engagement with said internal threads in said engaged position of said external restricting means.

17. A locking syringe as recited in claim 16, wherein said external threads are noncontinuous.

18. A locking syringe as recited in claim 16, wherein movement of said internal restricting means between said engaged and said disengaged positions thereof is at an angle to the longitudinal axis of said barrel which is less than or equal to the angle defined by the teeth of the said internal threads relative to the longitudinal axis with said barrel, whereby movement of said internal restricting means may be effected without causing appreciable corresponding longitudinal movement of said plunger within said barrel.

19. A locking syringe as recited in claim 1, wherein said trigger means comprises:

(a) a first channel; and (b) a first ramp in registry and in sliding engagement with said first channel, said first ramp being slidable within said first channel as said trigger means moves between said first and second positions thereof.

20. A locking syringe as recited in claim 19, wherein said trigger means further comprises:

(a) a second channel;

(b) a gusset disposed between said first and second channels; and (c) a second ramp in register and in sliding engagement with said second channel, said second ramp sliding within said second channel as said trigger means moves between said first and second positions thereof.

21. A locking syringe as recited in claim 20, wherein said first and second ramps and said first and second channels cant at an acute angle to the longitudinal axis of said barrel, and said acute angle defines the angle of the movement of said external restricting means between said engaged and said disengaged positions thereof.

22. A locking syringe as recited in claim 19, wherein adjacent first channel is a protruding arm in sliding engagement with first ramp, said protruding arm guiding the sliding engagement of said first ramp within said first channel.

23. A locking syringe as recited in claim 1, wherein said external restricting means is disposed along a spine connected to and moveable with said trigger means.

24. A locking syringe as recited in claim 23, further comprising:
(a) a handle rigidly secured to said plunger;
(b) a neck portion of said handle disposed proximate to said plunger; and
(c) an elongated groove formed in said neck portion of said handle, said spine being slidably disposed in said groove.

25. A locking syringe as recited in claim 24, wherein in said second position of said trigger means said spine is fully retracted into said groove in said neck portion of said handle, whereby no portion of said external restricting means protrudes radially beyond the outside edge of said groove.

26. A locking syringe as recited in claim 25, wherein said locking means comprises a resilient clamp selectively attachable about said neck portion of said handle in said second position of said trigger means traversing said groove to prevent said spine from engaging in movement to protrude radially beyond the outside edge of said groove.

27. A locking syringe as recited in claim 18, wherein said trigger means comprises:
(a) a first channel formed on said spine; and
(b) a first ramp disposed on said neck portion of said handle in register and in sliding engagement with said first channel, said first ramp sliding within said first channel as said trigger means moves between said first and second positions thereof.

28. A locking syringe as recited in claim 25, further comprising a plurality of channels disposed on said spine and situated in pairs in lateral register, said channels in each pair thereof being separated by a support gusset.

29. A locking syringe as recited in claim 28, further comprising:
(a) a first ramp in register and in sliding engagement with one of said channels; and
(b) a bevelled edge formed on said first ramp to facilitate the sliding engagement of said first ramp within said channel.

30. A locking syringe as recited in claim 29, further comprising a wedge disposed on said spine adjacent one of said channels, said wedge engaging said bevelled edge of said first ramp in substantially flush abutment.

31. A locking syringe as recited in claim 1, further comprising a stop means for restricting said plunger from movement into said barrel beyond a predetermined point of insertion.

32. A locking syringe as recited in claim 31, wherein said stop means is disposed on the external surface of said plunger.

33. A locking syringe as recited in claim 1, further comprising a cap connected to said barrel at the plunger end thereof.

34. A locking syringe as recited in claim 33, further comprising a collar on said plunger, said collar abutting the interior of said cap to prevent said plunger from being fully withdrawn from said barrel.

35. A locking syringe as recited in claim 1, further comprising means for increasing the force with which said external restricting means engages said internal restricting means in proportion to the pressure within said barrel exerted on said plunger.

36. A locking syringe comprising:
(a) a barrel;
(b) a cap attached to one end of said barrel;
(c) a plunger extending through said cap and being at least partially disposed within said barrel, said plunger engaging the interior of said barrel and being capable of reciprocating sliding movement therein;
(d) internal restricting means located within said cap;
(e) external restricting means located along at least a portion of the longitudinal axis of said plunger, said external restricting means being movable between an engaged position in which said external restricting means engages said internal restricting means to restrict reciprocating sliding movement of said plunger and a disengaged position in which said external restricting means is free of said internal restricting means and said plunger is capable of reciprocating sliding movement.
(f) trigger means for selectively retracting said external restricting means between said engaged and said disengaged positions thereof, said trigger means being capable of assuming a first position in which said external restricting means is placed in said engaged external engagement means is placed in said disengaged position thereof;
(g) plunger movement bias means for urging said external restricting means into said engaged position thereof; and
(h) locking means for preventing movement of said trigger means into said first position thereof, thereby to maintain said external restricting means in said disengaged position thereof and to permit reciprocating sliding movement of said plunger.

37. A locking syringe as recited in claim 36, further comprising means for increasing the force with which said external restricting means engages said internal restricting means in proportion to the pressure within said barrel exerted on said plunger.

38. A locking syringe as recited in claim 36, further comprising a pressure sensing means for sensing the pressure of the contents within said barrel.

39. A locking syringe as recited in claim 38, wherein said pressure sensing means is disposed at the end of said barrel opposite from said cap.

40. A locking syringe as recited in claim 36, wherein said internal restricting means comprises internal threads located on a portion of the interior of said cap opposing said plunger, and said external restricting means comprises external threads located along at least a portion of the longitudinal axis of said plunger, said external threads making threaded engagement with said internal threads in said engaged position of said external restricting means.

41. A locking syringe as recited in claim 36, wherein said trigger means comprises:
(a) first and second channels;
(b) a gusset disposed between said first and second channels; and
(c) first and second ramps in register and in sliding engagement, respectively, with said first and second channels, said first and second ramps sliding within said first and second channels, respectively, as said trigger means moves between said first and second positions thereof.

42. A locking syringe as recited in claim 41, wherein said first and second channels and said first and second ramps cant at an acute angle to the longitudinal axis of said barrel, and said acute angle defines the angle of the movement of said external restricting means between said engaged and said disengaged positions thereof.

43. A locking syringe as recited in claim 36, wherein said external restricting means is disposed along a spine connected to and movable with said trigger means, and wherein said locking syringe further comprises a handle rigidly secured to said plunger by a neck portion of said handle, said neck portion having formed therein an elongated groove in which said spine is slidably disposed.

44. A locking syringe as recited in claim 43, wherein said trigger means comprises a retraction bar rigidly secured to said spine, said retraction bar being selectively movable relative to said handle between first and second positions corresponding, respectively, to said first and second positions of said trigger means.

45. A locking syringe as recited in claim 38, wherein said locking means comprises a pawl secured to one of said handle or said retraction bar, said pawl in said second position of said retraction bar being capable of being moved selectively into a locked position engaging the other of said handle or said retraction bar, said pawl in said locked position thereof preventing the movement of said retraction bar out of said second position thereof.

46. A locking syringe as recited in claim 45, wherein said pawl is pivotally mounted to said retraction bar and said locking means comprises a pawl receiving aperture formed in said neck of said handle, the free end of said pawl being entered into said pawl receiving aperture in said locked position of said pawl.

47. A locking syringe as recited in claim 46, wherein said pawl is longitudinally slidable along said retraction bar.

48. A locking syringe as recited in claim 45, wherein said pawl is removably secured to one of said handle or said retraction bar.

49. A locking syringe as recited in claim 38, wherein said locking means comprises a plug insertable into an aperture formed in said plunger and occupied by said retraction bar in said first position thereof, said plug when inserted into said aperture preventing movement of said retraction bar into said first position thereof.

50. A locking syringe as recited in claim 38, wherein said external restricting means is disposed along a spine connected to and movable with said trigger means, and wherein said trigger means comprises:
  (a) a handle rigidly secured to said plunger;
  (b) a neck portion of said handle disposed proximate to said plunger; and
  (c) an elongated groove formed in said neck portion of said handle, said spine being slidably disposed in said groove.

51. A locking syringe as recited in claim 50, wherein in second position of said trigger means said spine is fully retracted into said groove in said neck portion of said handle, whereby no portion of said external restricting means protrudes radially beyond the outside edge of said groove.

52. A locking syringe as recited in claim 51, wherein said locking means comprises a resilient clamp selectively attachable about said neck portion of said handle in said second position of said trigger means traversing said groove to prevent said spine from engaging in movement to protrude radially beyond the outside edge of said groove.

53. An angioplasty syringe for inflating and deflating an angioplasty balloon catheter and for maintaining therewithin a predetermined pressure created by relative movement of components of the syringe, the angioplasty syringe comprising:
  (a) a barrel, the contents of said barrel being in fluid communication with the balloon catheter;
  (b) pressure sensing means for sensing the pressure of the contents within said barrel;
  (c) a plunger at least partially disposed within said barrel engaging the interior thereof and being capable of reciprocating sliding movement therein;
  (d) internal restricting means located on a portion of said interior of said barrel;
  (e) external restricting means located along at least a portion of the longitudinal axis of said plunger, said external restricting means being movable between an engaged position in which said external restricting means engages said internal restricting means to restrict reciprocating sliding movement of said plunger and a disengaged position in which said external restricting means is free of said internal restricting means and said plunger is capable of sliding movement;
  (f) trigger means for selectively retracting said external restricting means between said engaged and said disengaged position thereof, said trigger means being capable of assuming a first position in which said external restricting means is placed in said engaged position thereof and a second position in which said external engagement means is placed in said disengaged position thereof, said trigger means comprising:
    (i) a handle rigidly secured to said plunger by a neck portion of said handle;
    (ii) a retraction bar rigidly secured to said external restriction means, said retraction bar being selectively movable relative to said handle between first and second positions corresponding, respectively, to said first and second positions of said trigger means; and
    (iii) retraction bar bias means for urging said retraction bar into said first position thereof;
  (g) means for increasing the force with which said external restricting means engages said internal restricting means in proportion to the pressure of the contents of said barrel; and
  (h) locking means for preventing movement of said trigger means into said first position thereof, thereby to maintain said external restricting means in said disengaged position thereof and to permit reciprocating sliding movement of said plunger without sustained activation of said trigger means by an operator of said angioplasty syringe.

54. An angioplasty syringe as recited in claim 53, wherein said bias means comprises a coil spring compressed between said handle and said retraction bar.

55. An angioplasty syringe as recited in claim 53, wherein said external restricting means is disposed along a spine connected to and movable with said retraction handle, and said locking syringe further comprises an elongated groove formed in said neck of said handle in which said spine is slidably disposed.

56. An angioplasty syringe as recited in claim 55, wherein in said second position of said trigger means said spine is fully retracted into said groove in said neck portion of said handle.

57. An angioplasty syringe as recited in claim 53, wherein said locking means comprises a pawl mounted to one of said handle or said retraction bar, said pawl in said second position of said retraction bar being capable of being moved selectively into a locked position engaging the other of said handle or said retraction bar, said pawl in said locked position thereof preventing the movement of said retraction bar out of said second position thereof.

58. An angioplasty syringe as recited in claim 57, wherein said pawl is pivotally mounted to said retraction bar and wherein a pawl receiving aperture is formed in said neck of said handle, the free end of said pawl in said locked position thereof being entered into said pawl receiving aperture.

59. An angioplasty syringe as recited in claim 58, wherein said pawl is removably secured to one of said handle or said retraction bar.

60. An angioplasty syringe as recited in claim 53, wherein said locking means comprises a plug insertable into an aperture formed in said plunger and occupied by said retraction bar in said first position thereof, said plug when inserted into said aperture preventing movement of said retraction bar into said first position thereof.

61. An angioplasty syringe as recited in claim 56, wherein said locking means comprises a resilient clamp selectively attachable about said neck portion of said handle in said second position of said trigger means traversing said groove to prevent said spine from engaging in movement to protrude radially beyond the outside edge of said groove.

62. An angioplasty syringe for inflating and deflating an angioplasty balloon catheter and for maintaining therewithin a predetermined pressure created by relative movement of components of the syringe, the angioplasty syringe comprising:
  (a) a barrel, the contents of said barrel being in fluid communication with the balloon catheter;
  (b) a cap attached to one end of said barrel;
  (c) a plunger extending through said cap and being at least partially disposed within said barrel, said plunger engaging the interior of said barrel and being capable of reciprocating sliding movement therein;
  (d) internal restricting means located within said cap;
  (e) external restricting means located along at least a portion of the longitudinal axis of said plunger, said external restricting means being movable between an engaged position in which that external restricting means engages said internal restricting means to restrict reciprocating sliding movement of said plunger and a disengaged position in which said external restricting means is free of said internal restricting means and said plunger is capable of reciprocating sliding movement;
  (f) plunger movement bias means for urging said external restricting means into said engaged position thereof;
  (g) trigger means for selectively retracting said external restricting means between said engaged and said disengaged position thereof, said trigger means being capable of assuming a first position in which said external restricting means is placed in said engaged position thereof and a second position in which said external engagement means is placed in said disengaged position thereof, said trigger means comprising:
    (i) a handle rigidly secured to said plunger; and
    (ii) a retraction bar rigidly secured to said external restricting means, said retraction bar being selectively movable relative to said handle between first and second positions corresponding, respectively, to said first and second positions of said trigger means; and
  (h) a pawl secured to one of said handle or said retraction bar, said pawl in said second position of said retraction bar being capable of being moved selectively into a locked position engaging the other of said handle or said retraction bar, said pawl in said locked position of said second position thereof.

63. An angioplasty syringe as recited in claim 62, wherein said pawl is pivotally mounted to said retracting bar.

64. An angioplasty syringe as recited in claim 63, further comprising a pawl receiving aperture formed in said neck portion of said handle, the free end of said pawl being entered into said pawl receiving aperture in said locked position of said pawl.

65. An angioplasty syringe as recited in claim 64, wherein said pawl is longitudinally slidably along said retraction bar.

66. An angioplasty syringe as recited in claim 62, wherein said pawl is removably secured to one of said handle or said retraction bar.

67. An angioplasty syringe as recited in claim 62, wherein one end of said pawl comprises a plug insertable into an aperture in said handle occupied by said retraction bar in said first position thereof, said plug when inserted into said aperture prevents movement of said retraction handle into said first position thereof.

68. A method for priming a locking syringe to remove gas bubbles from the fluid contents thereof, said method comprising the steps:
  (a) filling the syringe with fluid contents;
  (b) actuating a trigger to simultaneously:
    (i) release the plunger of the syringe from a restricted mode of operation in which reciprocating sliding movement of the plunger in the barrel of the syringe is prevented and
    (ii) place the plunger in a free mode of operation in which the plunger is capable of reciprocating sliding motion within the barrel;
  (c) activating a locking means for preventing deactuation of the trigger, thereby to maintain the plunger in said free mode of operation and to permit reciprocating sliding movement of the plunger in the barrel;
  (d) releasing the trigger means while said locking means remains activated, thereby to keep the plunger in the free mode of operation and permit reciprocating sliding movement of the plunger without actuation of the trigger;
  (e) urging the plunger into the barrel; and
  (f) manipulating the syringe to remove bubbles from the fluid contents therein.

69. A method as recited in claim 68, wherein said step of actuating said trigger comprises the step of overcoming the biasing force of a spring urging plunger into the restricted mode of operation.

70. A method as recited in claim 69, wherein said syringe comprises:

(a) internal restricting means located on a portion of the interior of said barrel; and
(b) external restricting means located along at least a portion of the longitudinal axis of the plunger, said internal restricting means being retractable between an engaged position in which said external restricting means engages said internal restricting means to restrict reciprocating sliding movement of said plunger and a disengaged position in which said external restricting means is free of said internal restricting means and said plunger is capable of reciprocating sliding movement.

71. A method as recited in claim 70, wherein said trigger comprises:
(a) a handle rigidly secured to said plunger; and
(b) a retraction bar rigidly secured to said external restricting means, said retraction bar being selectively movable relative to said handle between first and second positions corresponding, respectively, to said engaged and disengaged positions of said external restricting means.

72. A method as recited in claim 71, wherein said step of activating a locking means comprises the step of pivoting a pawl securing said handle or said retraction bar into a locked position engaging the other of said handle or said retraction bar.

73. A method as recited in claim 71, wherein said step of activating the locking means comprises the step of securing said pawl to one of said handle or said retraction bar.

74. A method as recited in claim 71, wherein said step of activating the locking means comprises the step of snapping a resilient clamp about said handle so as to preclude return of said retraction bar into said first position thereof.

75. A method as recited in claim 71, wherein said step of activating the locking means comprises the step of inserting a plug into an aperture in said handle occupied by said retraction bar in said first position thereof, thereby to prevent movement of said retraction bar into said first position.

* * * * *

UNITED STATES PATENT AND TRADEMARK OFFICE
CERTIFICATE OF CORRECTION

PATENT NO. : 5,209,732

DATED : May 11, 1993

INVENTOR(S) : FRED P. LAMPROPOULOS et al.

It is certified that error appears in the above-identified patent and that said Letters Patent is hereby corrected as shown below:

```
Column 4, line 32, "o" should be --of--
Column 7, line 26, after "retracted" insert --position;--
Column 7, line 54, after "of" insert --the--
Column 8, line 16, "includes" should be --include--
Column 11, line 50, after "properly" insert --.--
Column 14, line 61, "preventing" should be --prevents--
Column 15, line 8, "operator" should be --operation--
Column 15, line 47, "pawl receiving aperture" should be
--pawl receiving aperture 96--
Column 16, line 21, delete "24"
Column 17, line 60, "removable" should be --removably--
```

Signed and Sealed this

Sixteenth Day of August, 1994

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,209,732
DATED : May 11, 1993
INVENTOR(S) : FRED P. LAMPROPOULOS et al.

It is certified that error appears in the above-indentified patent and that said Letters Patent is hereby corrected as shown below:

Column 17, line 20, claim 1, replace "engagement" with --restricting--
Column 18, line 35, claim 18, replace "internal" with --external--
Column 18, line 40, claim 18, replace "internal" with --external--
Column 20, line 30, claim 36, replace "engagement" with --restricting--
Column 20, line 30, claim 36, after "engaged" insert --position thereof and a second position in which said--
Column 22, line 35, claim 53, replace "engagement" with --restricting--
Column 23, line 53, claim 62, change "that" to read --the--
Column 24, line 1, claim 62, replace "engagement" with --restricting--
Column 24, line 65, claim 69, after "urging" insert --said--
Column 25, line 5, claim 70, replace "internal" with --external--

Signed and Sealed this

Fifteenth Day of April, 1997

Attest:

BRUCE LEHMAN

*Attesting Officer*   *Commissioner of Patents and Trademarks*